(12) United States Patent
Schneider et al.

(10) Patent No.: US 11,890,456 B2
(45) Date of Patent: Feb. 6, 2024

(54) SELF-ADMINISTERED INJECTION DEVICE AND METHOD

(71) Applicant: DJ Medical, LLC, Burnsville, MN (US)

(72) Inventors: Daniel Schneider, Minneapolis, MN (US); Jay Duckson, Mendota, MN (US)

(73) Assignee: DJ MEDICAL, LLC, Burnsville, MN (US)

( * ) Notice: Subject to any disclaimer, the term of this patent is extended or adjusted under 35 U.S.C. 154(b) by 45 days.

(21) Appl. No.: 15/815,026

(22) Filed: Nov. 16, 2017

(65) Prior Publication Data

US 2018/0133403 A1   May 17, 2018

Related U.S. Application Data

(60) Provisional application No. 62/532,052, filed on Jul. 13, 2017, provisional application No. 62/422,686, filed on Nov. 16, 2016.

(51) Int. Cl.
  *A61M 5/28* (2006.01)
  *A61M 5/42* (2006.01)
  (Continued)

(52) U.S. Cl.
  CPC ............ *A61M 5/281* (2013.01); *A61K 8/66* (2013.01); *A61K 9/0019* (2013.01); *A61K 9/08* (2013.01);
  (Continued)

(58) Field of Classification Search
  CPC ............ A61K 9/0019; A61M 5/31573; A61M 5/3202; A61M 5/3257; A61M 5/3287;
  (Continued)

(56) References Cited

U.S. PATENT DOCUMENTS

| 5,137,516 A | 8/1992 | Rand et al. |
| 2008/0119958 A1* | 5/2008 | Bear .................... A61J 7/0481 700/244 |

(Continued)

FOREIGN PATENT DOCUMENTS

| GB | 2447046 | 7/2011 |
| WO | 03068290 | 8/2003 |

(Continued)

OTHER PUBLICATIONS

International Search Report and Written Opinion for related PCT Application PCT/US2017/062000 dated Feb. 14, 2018 (18 pages).

(Continued)

*Primary Examiner* — Bhisma Mehta
*Assistant Examiner* — Nidah Hussain
(74) *Attorney, Agent, or Firm* — Winthrop & Weinstine, P.A.; Nadeem W. Schwen; Alicia Griffin Mills

(57) ABSTRACT

An injection device kit for the self-administration of an injection of solution that includes a body portion configured for engagement with a cartridge containing the solution and an injection needle where the body portion includes an injection component having an actuation mechanism for inserting the injection needle of the cartridge and for injecting the solution in the cartridge and a safety mechanism on the body portion and configured to prevent injection unless released.

17 Claims, 27 Drawing Sheets

(51) Int. Cl.

| | |
|---|---|
| *A61M 5/315* | (2006.01) |
| *A61M 5/32* | (2006.01) |
| *A61M 5/20* | (2006.01) |
| *A61M 5/00* | (2006.01) |
| *A61Q 19/08* | (2006.01) |
| *A61M 5/31* | (2006.01) |
| *A61M 5/46* | (2006.01) |
| *A61M 5/24* | (2006.01) |
| *A61K 8/66* | (2006.01) |
| *A61K 9/00* | (2006.01) |
| *A61K 9/08* | (2006.01) |
| *A61K 38/48* | (2006.01) |

(52) U.S. Cl.
CPC ......... *A61K 38/4893* (2013.01); *A61M 5/002* (2013.01); *A61M 5/008* (2013.01); *A61M 5/2033* (2013.01); *A61M 5/31511* (2013.01); *A61M 5/31571* (2013.01); *A61M 5/31573* (2013.01); *A61M 5/3202* (2013.01); *A61M 5/3257* (2013.01); *A61M 5/3287* (2013.01); *A61M 5/427* (2013.01); *A61Q 19/08* (2013.01); *C12Y 304/24069* (2013.01); *A61K 2800/87* (2013.01); *A61K 2800/91* (2013.01); *A61M 5/003* (2013.01); *A61M 5/24* (2013.01); *A61M 5/31551* (2013.01); *A61M 5/31563* (2013.01); *A61M 5/31595* (2013.01); *A61M 5/326* (2013.01); *A61M 5/425* (2013.01); *A61M 5/46* (2013.01); *A61M 2005/005* (2013.01); *A61M 2005/206* (2013.01); *A61M 2005/208* (2013.01); *A61M 2005/2013* (2013.01); *A61M 2005/2073* (2013.01); *A61M 2005/2414* (2013.01); *A61M 2005/3139* (2013.01); *A61M 2205/58* (2013.01)

(58) Field of Classification Search
CPC ........ A61M 5/427; A61M 5/003; A61M 5/24; A61M 5/31563; A61M 2005/005; A61M 2005/2013; A61M 2005/2026; A61M 2005/202; A61M 2005/2073; A61M 2005/208; A61M 5/002; A61M 5/008
USPC ...................................................... 604/506
See application file for complete search history.

(56) References Cited

U.S. PATENT DOCUMENTS

| | | | | |
|---|---|---|---|---|
| 2010/0292642 | A1* | 11/2010 | Kurup | .................. A61F 9/0017 |
| | | | | 604/116 |
| 2012/0221036 | A1 | 8/2012 | Ahmann | |
| 2013/0281936 | A1* | 10/2013 | Kemp | .................... A61M 5/28 |
| | | | | 604/197 |
| 2014/0324021 | A1* | 10/2014 | Ulrich | ................... G16H 40/67 |
| | | | | 604/506 |
| 2015/0201880 | A1* | 7/2015 | Bureau | .................. A61M 5/20 |
| | | | | 600/300 |
| 2016/0228642 | A1 | 8/2016 | Cowe | |
| 2016/0287788 | A1 | 10/2016 | Tremblay et al. | |
| 2016/0331900 | A1* | 11/2016 | Wei | ...................... A61M 5/326 |
| 2017/0281877 | A1* | 10/2017 | Marlin | ................ A61M 5/3234 |
| 2017/0340840 | A1* | 11/2017 | Sweis | .................. A61M 5/427 |
| 2018/0147352 | A1 | 5/2018 | Farmer et al. | |

FOREIGN PATENT DOCUMENTS

| | | |
|---|---|---|
| WO | 2010018411 | 2/2010 |
| WO | 2017220553 | 12/2017 |

OTHER PUBLICATIONS

International Search Report for related International Application No. PCT/US2021/013332, dated Mar. 25, 2021, 3 pages.
Written Opinion for related International Application No. PCT/US2021/013332, dated Mar. 25, 2021, 5 pages.
Communication Pursuant to Article 94(3) EPC for corresponding EP application No. 17812122.4 dated Sep. 10, 2020, 8 pages.

* cited by examiner

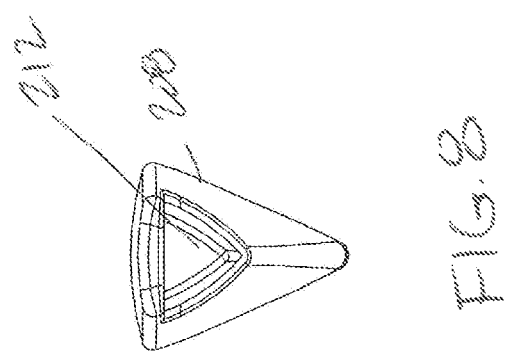

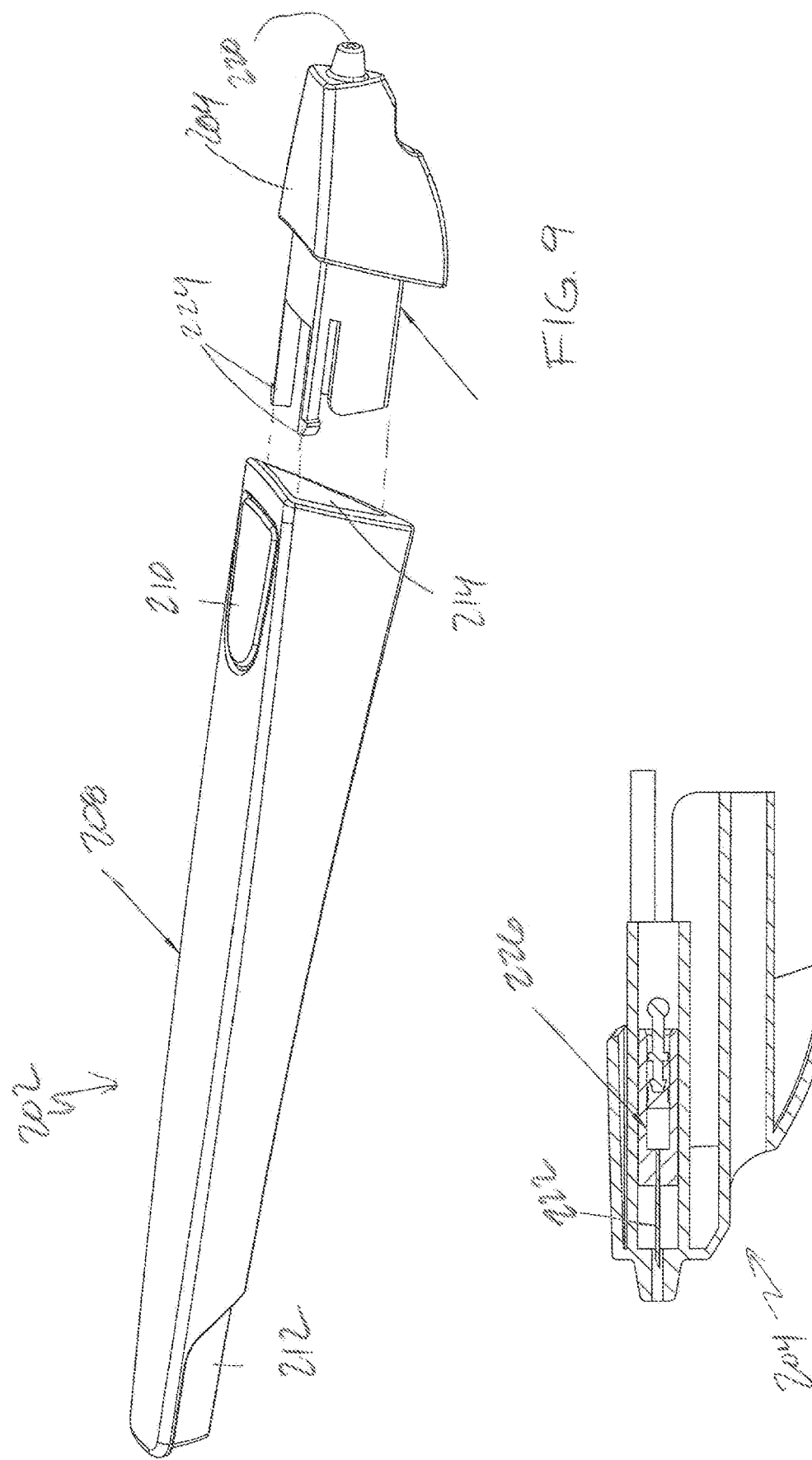

| Step | Basic Process |
|---|---|
| 1 | Doctor prescribes/orders Botox |
| 2 | Botox is activated by manufacturer and shipped |
| 3 | Botox ships to treatment location |
| 4 | Refrigerate until use |
| 5 | Retrieve set/setup cartidges |
| 6 | Apply numbing cream to injection sites |
| 7 | Apply injection map to patient injection sites |
| 8 | Set Hammer |
| 9 | Load 1st cartridge |
| 10 | Remove safety cap/foil seal |
| 11 | Locate injector at 1st injection site |
| 12 | Compress safety mechanism |
| 13 | Inject/release injection mechanism |
| 14 | Reset Hammer |
| 15 | Remove cartridge/dispose of needle |
| 16 | Remove injection map |
| 17 | Dispose of system |
| 18 | Clean injector |

FIG. 20

SELF-ADMINISTERED INJECTION DEVICE AND METHOD

CROSS-REFERENCE TO RELATED APPLICATIONS

The present application claims priority to U.S. Provisional Application 62/422,686 entitled Systems and Methods for Self-Administration of Botulinum Toxin, filed on Nov. 16, 2016 and 62/532,052 entitled Systems and Methods for Self-Administration of Botulinum Toxin, filed on Jul. 13, 2017, the contents of which are incorporated by reference herein in their entireties.

FIELD OF THE INVENTION

The present application relates to a method and system for user, lay person, and/or self-administration of an injectable substance such as insulin, botulinum toxin, chronic illness treatment medicines, flu shots, or other medicinal or cosmetic treatment substances. More particularly, the present application relates to a method and system for self-administration of an injectable substance at or around the facial area. Still more particularly, the present application relates to a method and system for self-administration of an injectable substance at or near the eye and forehead area.

BACKGROUND

In many contexts, injections of medicine are performed by trained professionals. For example, vaccinations, flu shots, antibiotics, and other medicines are commonly administered by nurses, physician assistants, doctors, or other trained professionals. In some cases, where injection of medicine is performed on a regular or relatively frequent periodic basis, patients may learn to administer injections on their own. For example, individuals with diabetes may learn to regularly administer insulin to control insulin levels in their system. These individuals may also regularly test their insulin levels to determine whether there is a need for an injection. Other examples include patients with chronic illnesses such as multiple sclerosis, for example. In these contexts, the patient may become relatively well versed in the injection process due to the repetition of the procedure.

Botulinum toxin is a substance used for various purposes, including medical purposes for treating various medical conditions such as hyperhidrosis and migraine headaches, as well as cosmetic purposes. In some cosmetic applications, botulinum toxin is used to relax muscles, such as facial muscles, in order to reduce lines or wrinkles in the skin or otherwise smooth the appearance of skin. In other applications, botulinum toxin may be used to prevent or help prevent the formation of lines or wrinkles on the face or another body part. Botulinum toxin, which may be provided under the brand name BOTOX, DYSPORT, XEOMIN, or other names, is typically applied by injection. A syringe may be filled with a desired amount of the botulinum toxin and injected into a muscle or other tissue. Botulinum toxin may be used to decrease wrinkles or otherwise smooth the appearance of skin around an individual's eyes, forehead, mouth, neck, scalp, or other areas of the face or body. Generally, botulinum toxin injected for medical or cosmetic purposes is injected by a medical professional, such as a physician or a nurse or aesthetician practicing under the guidance of a physician.

Like many medicinal drugs or substances, cosmetic treatments such as botulinum toxin are commonly administered by trained professionals. This is, in part, because the location of the administration is important with respect to the aesthetic effect of the injection. Still further, the amount of the injected substance also affects the resulting cosmetic result. Moreover, these types of injections are not commonly performed on a frequent basis and, as such, the patient does not have the opportunity to become comfortable with the process.

SUMMARY

The present application, in one or more embodiments, may include an injection device for self-administering of an injection of solution. The device may include a body portion configured for engagement with a cartridge containing the solution and an injection needle. The body portion may include an injection component having an actuation mechanism for inserting the injection needle of the cartridge and for injecting the solution in the cartridge. The device may also include a safety mechanism arranged on the body portion and configured to prevent injection unless released.

In one or more embodiments, a method of self-administering an injection of solution may include positioning an injection patch or template on a body area and engaging a cartridge with an injection device to select the cartridge from a tray. The cartridge may contain the solution that is to be injected. The method may also include aligning the injection device and the cartridge with a location indicator on the injection patch or template and pressing the injection device against the body thereby releasing a safety mechanism. The method may also include depressing a trigger on the injection device thereby inserting a needle of the cartridge and injecting the solution.

In one or more embodiments, a cartridge for use with an injection device may include a chamber configured for holding a solution and a needle in fluid communication with the chamber. The cartridge may also include a plug arranged in a trailing end of the chamber and configured for forced movement through the chamber to eject the solution from the chamber through the needle. The cartridge may also include an engagement mechanism configured for pressing engagement by the injection device to secure the cartridge to the injection device and in alignment with a plunger for actuation of the plug by the plunger.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

FIG. 1 is a front view of a user's forehead, showing approximate locations for botulinum toxin injections, according to one or more embodiments.

FIG. 2 is a side view of a user's eye area, showing approximate locations for botulinum toxin injections, according to one or more embodiments.

FIG. 3A is a perspective view of a kit including an injection device and a staging tray including a plurality of cartridges, according to one or more embodiments.

FIG. 3B is a cross-sectional view thereof.

FIG. 4 is a perspective view of an injection devices of the present disclosure, according to one or more embodiments.

FIG. 5 is a side view of the injection devices of FIG. 4, according to one or more embodiments.

FIG. 6 is a top view of the injection devices of FIG. 4, according to one or more embodiments.

FIG. 8 is a release button end view of the injection devices of FIG. 4, according to one or more embodiments.

FIG. 9 is a perspective view of an injection device of the present disclosure, with a cartridge portion separated from a body portion.

FIG. 10 is a cross sectional view of a cartridge portion of an injection device of the present disclosure, according to one or more embodiments.

FIG. 20 shows a work flow method of the present disclosure, according to one or more embodiments.

DETAILED DESCRIPTION

The present disclosure, in one or more embodiments, relates to systems and methods for self-administration of botulinum toxin injections. Particularly, the present disclosure, in one or more embodiments, relates to an injection device, a kit including the injection device and other accoutrements, and a method for using the device and/or kit. The injection device may be particularly adapted for use by the relatively untrained user and may provide for easy loading of pre-filled cartridges and safety mechanisms associated with exposing the needle and injecting the included substance. The kit may include a series of cartridges each containing a particular quantity of botulinum toxin, the injection device, a staging tray for arranging the cartridges before use, and a series of injection patches. The additional portions included in the kit may further the ability for a user to self-administer botulinum toxin without training or frequent use. In particular, the cartridges in the kit may have secluded or hidden needles for purposes of safety, but also avoiding viewing for users uncomfortable with needles. The cartridges may also be preloaded/dosed cartridges such that dosing is simple and straight forward. The cartridges and the injection device may work together for a simple reloading process and the staging tray may allow for arrangement of the cartridges in an area and/or order for ease of use. Finally, the injection patches/template may work with the injection device to help position the injection device prior to injection and the template may include a numbing agent to reduce pain or injection sensation. Accordingly, the device and/or kit may be used to self-administer botulinum toxin injections on a relatively infrequent basis, with ease, efficiently, with low anxiety, low pain, and with high precision and accuracy. It is to be appreciated that while much of the present disclosure is focused on botulinum toxin injections, other injections may be performed with some or all of the devices described herein.

Figure 1:
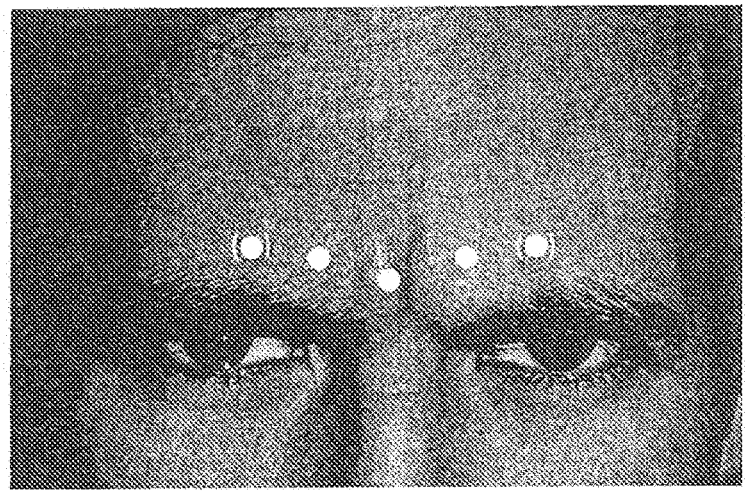
Figure 2:
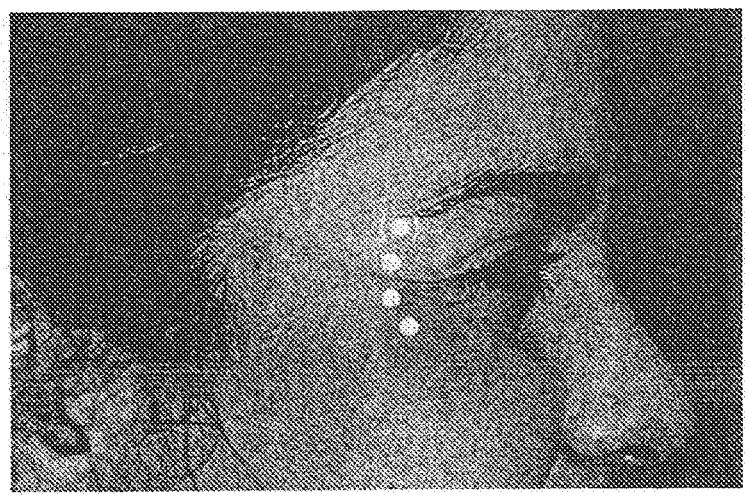

Referring now to FIGS. 1 and 2, the present application, in one or more embodiments, relates to a device, kit, and/or method for self-administered botulinum toxin injections. FIGS. 1 and 2 illustrate some locations where a user may wish to self-inject botulinum toxin. A user may wish to inject botulinum toxin near the user's eye(s), forehead, neck, scalp, and/or any other suitable location. Still other locations may be suitable for injection and still other substances may be injected using a same or similar device and/or kit as described herein.

Figure 3B:
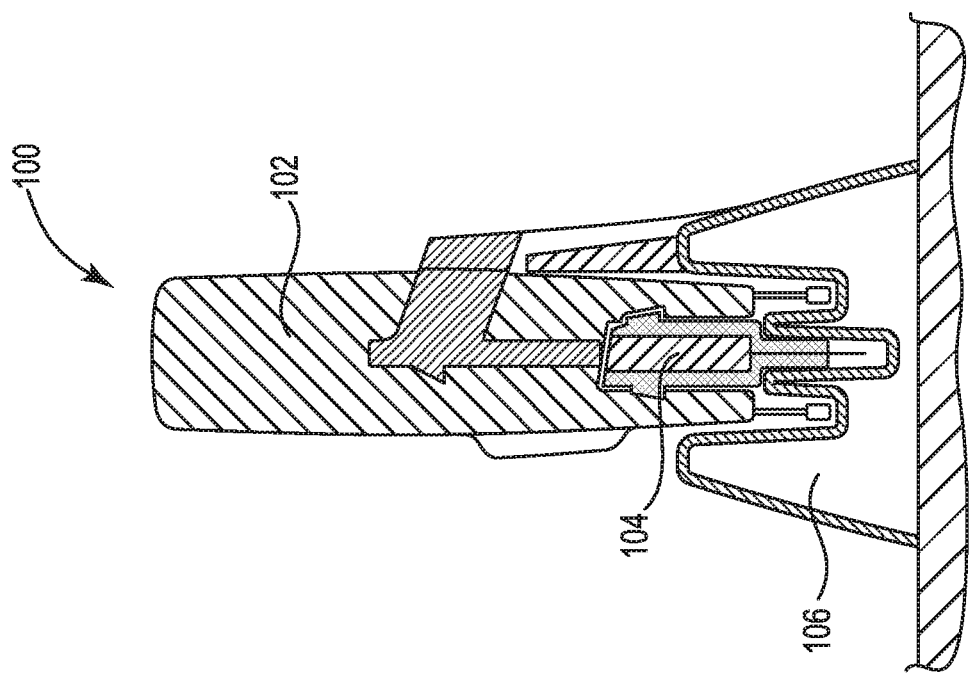
Figure 3A:
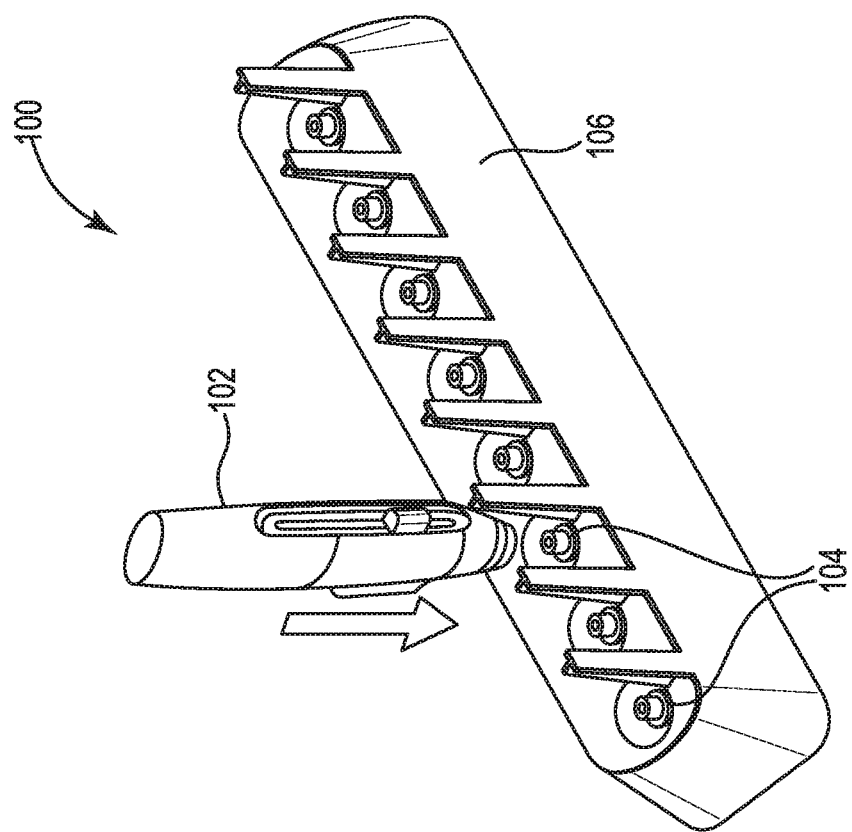
Figure 4:
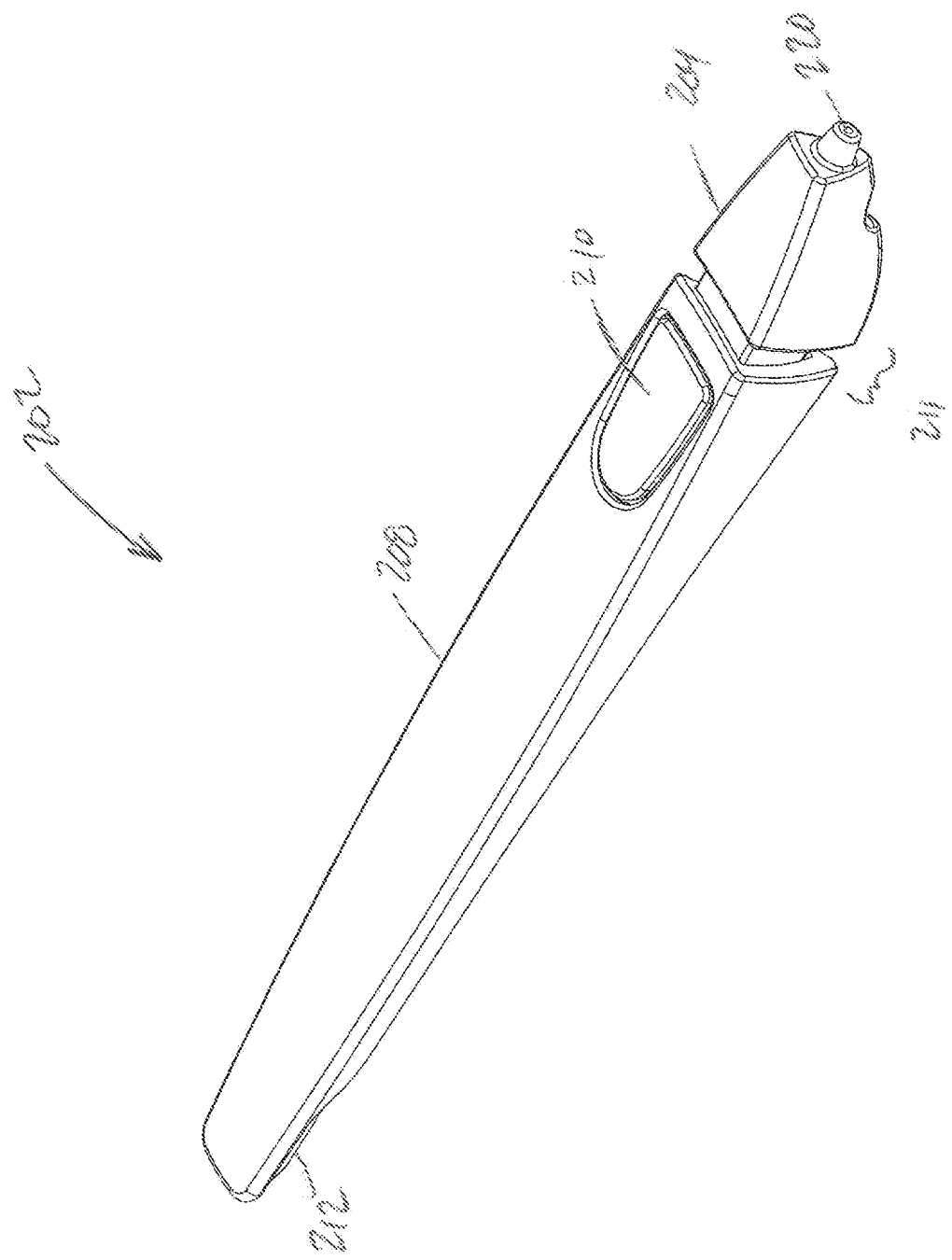
Figure 5:
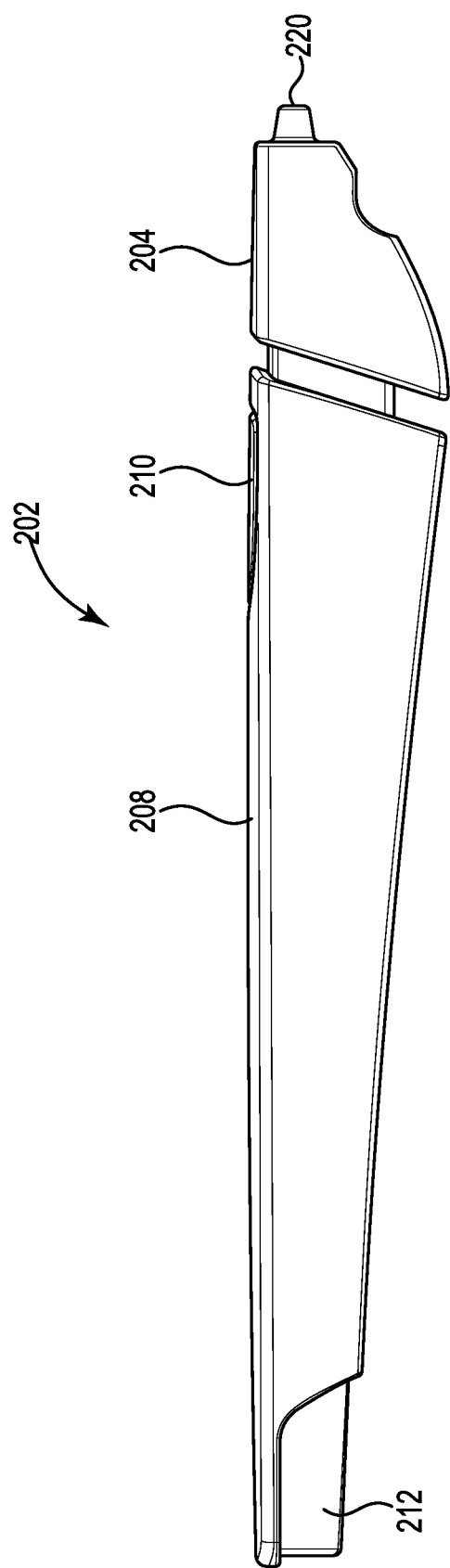
Figure 6:
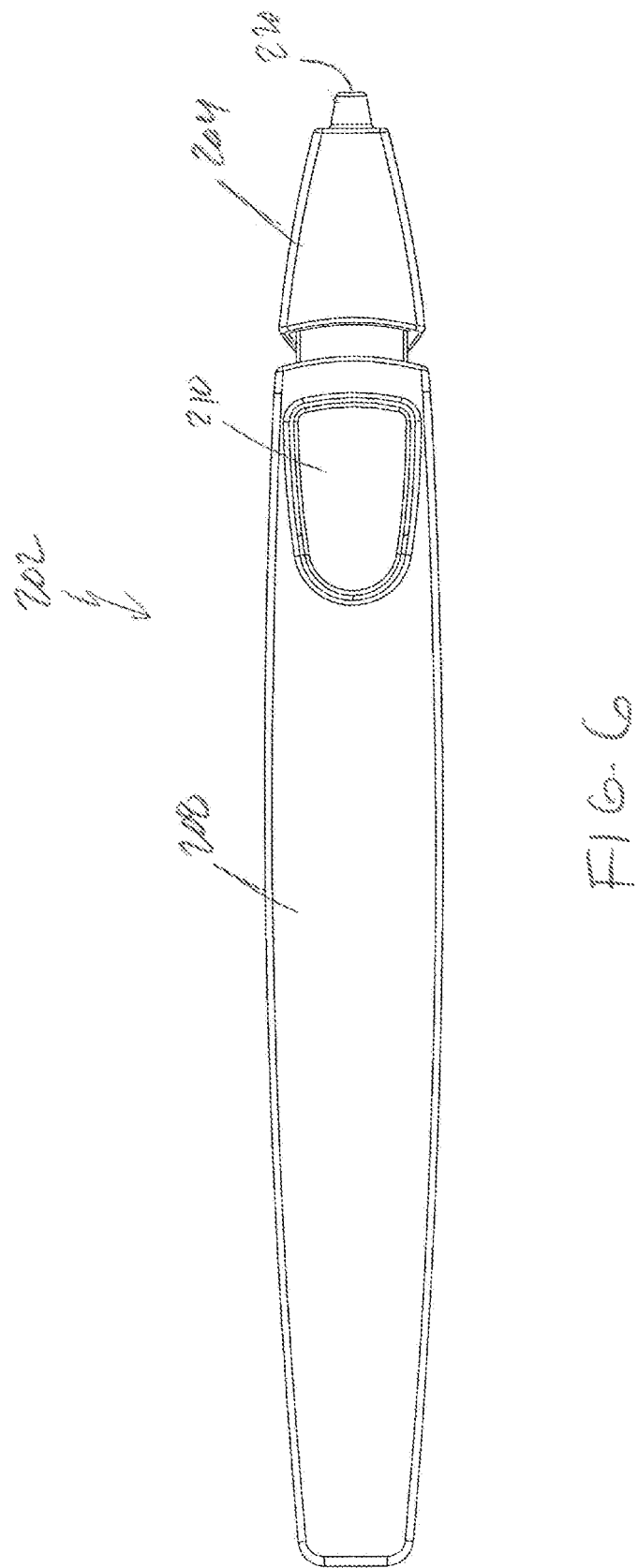
Figure 7:
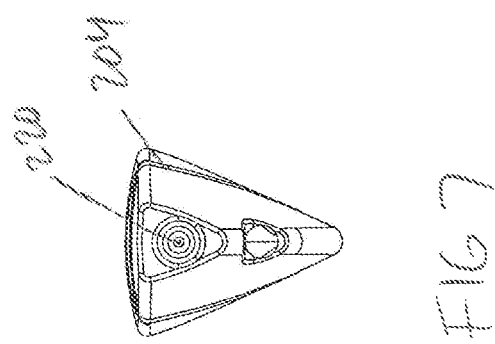
FIG. 7 is an injection end view of the injection devices of FIG. 4, according to one or more embodiments.

One example of at least some portions of a kit 100 according to one or more embodiments is shown in FIGS. 3A and 3B. As shown, the kit may include an injection device 102, a series of cartridges 104, and a staging template or tray 106. As mentioned, and while not shown, the kit may also include a series of injection patches or templates 108.

Injection Device

One example of an injection device 202 and cartridge 204 is shown in FIGS. 4-13. While differing from injection device 102 and cartridge 104 in form, the features and functions of injection devices 102 and 202 and the cartridges 104 and 204 may be the same and/or similar. As shown, the injection device 202 may include a body portion 208, an injection component, a safety component 211, and a release component 212. The injection device 202 may be configured to selectively engage cartridges in the tray, position the cartridge on a location of a user, and inject the solution in the cartridge. Positioning of the cartridge may be aided by an injection patch and the safety mechanism may prevent injection unless/until proper positioning and/or pressure are applied to the injection device. Upon proper positioning and pressure, the injection device may be configured to insert a needle from within the cartridge and, upon full insertion of the needle, inject the solution stored in the cartridge. The cartridge may then be ejected from the injection device preparing the injection device for engagement of another cartridge.

The body portion 208 of the injection device may be configured and/or sized for a comfortable fit in a human hand and, as such, may be sized shaped or molded like a baton, stick, handle, or other relatively comfortable shape for grasping by the human hand. In one or more embodiments, the body portion 208 may generally have an elongated pen-like length and size. In one or more embodiments, the body portion 208 may have a generally triangular cross sectional shape. The body portion 208 may include one or more ergonomic features.

The body portion may also form an enclosure for the injection component and a base for positioning of triggers and/or release buttons. The body portion 208 may also facilitate engagement between the cartridge 204 and the injection component. For example, as shown in FIG. 9, the body portion 208 may have an opening 214 configured to receive the cartridge portion 204. The body portion 208 may have an injection button 210 or other component configured to both insert a needle within the cartridge 204 and inject the solution contained in the cartridge 204. As shown in FIGS. 4-13, the body portion 208 may additionally have a release button 212 configured to release or decouple the cartridge 204 from the body portion 208.

The injection component may be housed within the body portion 208 and may include a trigger 210 and an injection spring and/or a series of springs configured for advancing a hammer and/or a plunger to manage the injection. The trigger 210 may include a button or other depressible or sliding element that releases the springs to advance the hammer and/or plunger or both. In other embodiments, the trigger 210 may hold back the hammer, the plunger, or both and actuating the trigger may release the hammer/plunger or both. The injection component may be configured to avoid injection unless a safety mechanism has been released. The injection component may also be configured to fully insert the needle of the cartridge first followed by depressing of a plunger within the cartridge to inject the contained solution. In this manner, inadvertent needle sticks, and inadvertent dispensing of the solution may be avoided. To this end, the injection component may include a two stage system configured to perform a two stroke operation if/when the safety mechanism is released.

Figure 11:
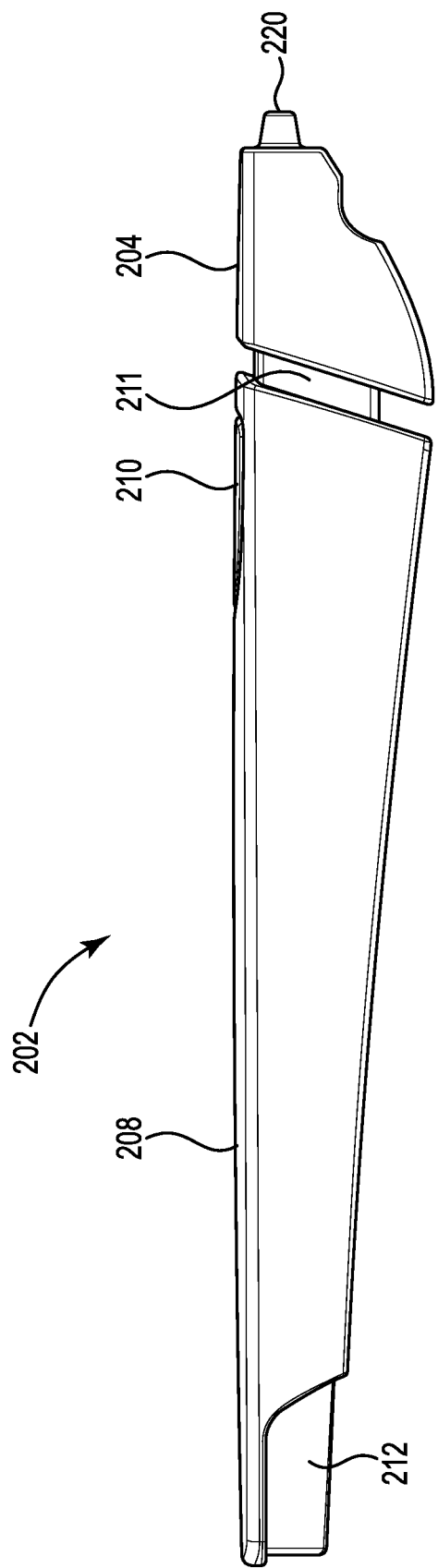
FIG. 11 is a side view of an injection device of the present disclosure, with a cartridge portion in a first position.
Figure 12:
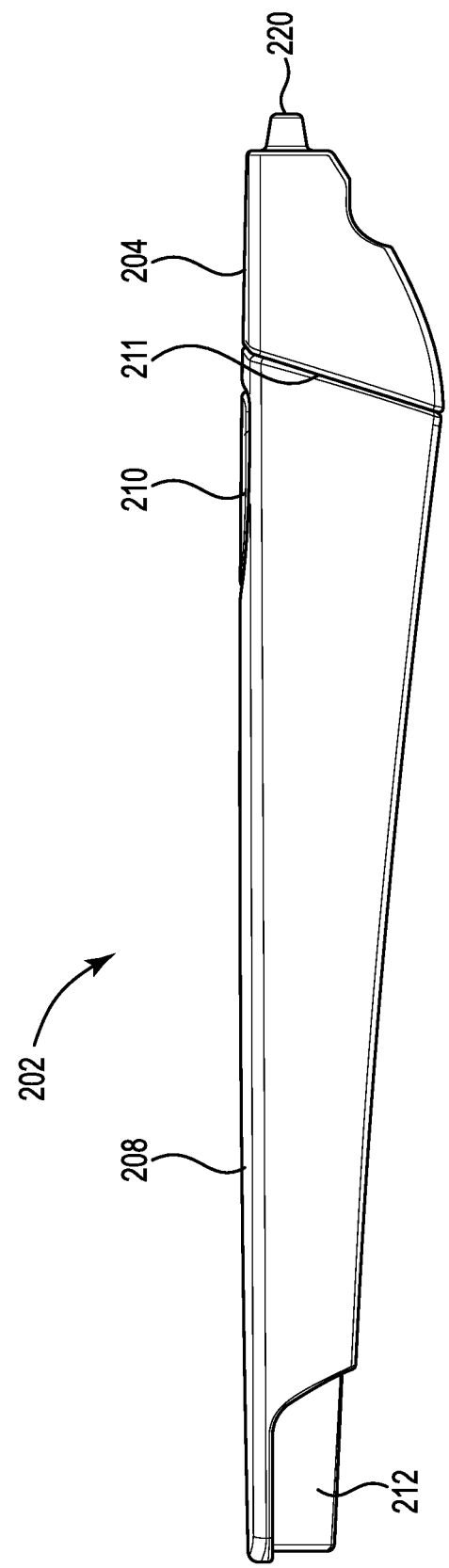
FIG. 12 is a side view of the injection device of FIG. 11, with the cartridge portion in a second position.
Figure 13:
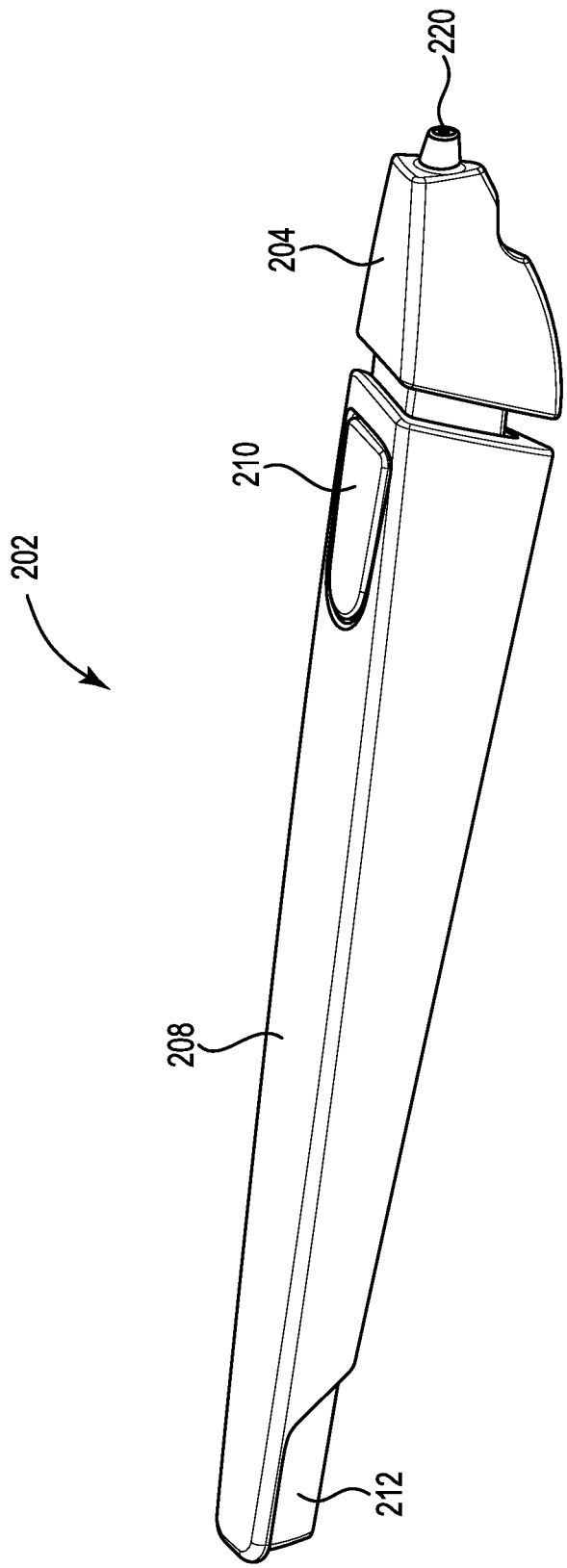
FIG. 13 is a perspective view of an injection device of the present disclosure.

As shown in FIGS. 11 and 12, the safety mechanism 211 may be provided at the engagement interface between the cartridge 204 and the body portion 208. In this embodiment, the body portion may be used to engage the cartridge while leaving a gap between two abutting surfaces of the body portion 208 and cartridge 204. The injection component may be prevented from functioning unless/until the two abutting surfaces come into contact with one another. Typically, this may occur when the user presses the tip of the cartridge against their skin just prior to injection. As the user presses the tip of the cartridge against their skin, the cartridge may further engage the body portion 208 and trigger an internal mechanical or electrical switch, which allows the injection component to function. In one or more embodiments, for example, the internal switch may include a chamfered, beveled, or cam surface that causes a blocking element to slide radially outward due to the intruding cartridge. The blocking element, having slid radially outward, may slide out of the way of the injection component causing the injection component to become "live" so to speak. Other types of mechanical switches may also be used such as switches that block trigger motion rather than the injection component motion. Still other approaches may also be used. Electrical switches may be used where the intruding cartridge creates or interrupts an electrical contact, which allows the injection component to become live. Still other approaches using electrical switches may be used. Moreover, while the safety mechanism has been described as being related to the interface between the cartridge and the body portion, other locations may be provided. For example, the safety mechanism may be provided entirely on the cartridge where activation of the injection component on the body portion is simply not strong enough to overcome the resistance of the safety component on the cartridge. Still other approaches and locations of the safety component may be provided.

In one or more embodiments, the injection component may include a hammer and a plunger each driven by separate springs, biasing mechanisms, or other advancing mechanisms. The hammer may be configured to insert the needle.

As such, the hammer may be configured to engage a trailing end of a needle portion of the cartridge and advance along the inside of the body portion for a stroke length equal to any needle offset distance from the skin and the needle depth. The needle offset distance may be defined by the distance from the surface engaging tip of a needle shroud 220 on the cartridge back to the tip of the needle 222. The needle depth may be defined by the depth at which the injection is to take place. For botulinum toxin injections, the depth may be relatively shallow, while other injections may call for deeper needle penetration. The cartridge and/or injection device may be calibrated or designed to accommodate a suitable needle penetration. The hammer may be positioned within the body portion and may include a series of guides and stops allowing the hammer to travel along the inside of the body portion for the particular stroke length.

The plunger may travel along with the hammer portion and may be configured to force the solution contained in the cartridge through the needle once the needle has been fully inserted into the skin. In one or more embodiments, the travel of the hammer may function similar to the safety mechanism described above by preventing fluid ejection until the full hammer stroke has been performed. That is, advancement of the hammer may engage a beveled, chamfered, or cam surface, for example, that moves a catch out of the way of the plunger. When the catch is moved clear of the plunger, the biasing mechanism forcing the plunger forward may cause the plunger to engage a cork, slide, or stopper through a cylinder causing the solution to flow through the needle into the skin. In other embodiments, the plunger may travel in isolation from the hammer. For example, the hammer may be sleeved around the plunger and may advance apart from the plunger and when the stroke of the hammer is complete, the plunger may be released. Still other arrangements of a hammer and a plunger may be provided.

The release component 212 may include a mechanism for releasing the cartridge 204 from the injection device. The release component 212 may include a depressible button or a sliding element or another actuation mechanism may be used. In one or more embodiments, the release component may be built into the trigger and may be part of the a portion of the trigger motion. That is, advancing a slide, for example, may actuate the injection component and once the injection is complete, advancing a slide further may eject the cartridge from the device. The release component may function in one or a combination of a variety of ways including pushing or biasing catches out of place allowing the cartridge to be released or forcibly pushing the cartridge itself from the device by overcoming an holding mechanism of the cartridge. Still other approaches to a release component many be provided.

In some embodiments, the injection device may be cocked or otherwise readied prior to use. For example, a user may push a button that causes the spring within the device to compress behind the syringe plunger, such that when the spring is released, it may push the plunger. In some embodiments, such cocking or readying of the injection device may be performed using a particular tool. For example, a tool may be inserted into the device to compress the spring before or after loading a syringe into the device. In other embodiments, the cocking or readying of the injection device may be performed by other means, such as by pushing a button or twisting, pulling, or sliding a portion of the device. In still other embodiments, the device may be configured such that it may be operated without the need for a cocking or readying step.

In one or more embodiments, as shown in FIGS. 3A and 3B, the hammer and/or plunger actuation system may be cocked or loaded, for example, by engagement with the tray 106. The injector device may have a handle portion configured to receive a cartridge portion. For example, the handle portion may have one or more slots or grooves configured to align with corresponding tabs of the cartridge portion. In some embodiments, a hammer, configured to align with a plunger, may extend from the handle portion. The hammer may be coupled to an injection button, such that pushing or pressing the injection button may cause the hammer to depress a plunger. In some embodiments, a cartridge array may provide a plurality of cartridge portions. In addition, in some embodiments, the cartridge array may have a hammer reset tower, and in some embodiments may have a hammer reset tower arranged proximate to each cartridge in the array. The array may be configured such that a user may align the handle portion with a cartridge portion in the array so as to insert the cartridge into the handle or otherwise couple the handle and cartridge together. The user may couple the cartridge to the handle by pressing the handle down onto the cartridge. As the user aligns the handle and a cartridge, the injection button of the handle may simultaneously be aligned with a hammer reset tower. As the user pushes the handle onto the cartridge portion to attach the cartridge portion, the hammer reset tower may act to push the injection button and/or hammer back, thus cocking or readying the hammer for an injection. In some embodiments, each cartridge portion may have a compressible safety mechanism configured to enclose around a syringe needle until compressed prior to or during injection.

Cartridge

The cartridges 204 may be configured for engagement with the injection device 202 and further engagement by the injection component of the injection device. That is, the cartridges may be configured for selective engagement and/or "picking" from a tray by the injection device. As shown in FIG. 9, for example, the cartridge may include a one or a plurality of flexible arms having catches 224 at the ends thereof. The arms may be aligned with slots in the injection device and slots may terminate at a cavity. As such, the injection device may be pressed onto the cartridge with the slots aligned with the arms. The catches may cause the arms to deflect allowing the catches to slide along the slots until the catches reach the respective cavities and snap into place. Still other engagement mechanisms between the cartridge and the injection device may be provided.

In any case, the engagement of the cartridge 204 with the injection device 202 may cause a fluid pod 226 to be juxtaposed to the hammer and/or plunger of the injection device so as to poise the fluid pod for injection. The fluid pod 226 may include a chamber configured for holding the injectable fluid, drug, or substance. The fluid pod may be in fluid communication with a needle secured adjacent to the fluid pod. The fluid pod may include a plug, slide, or other advancing mechanism at a trailing end thereof. The advancing mechanism may be configured to move through the chamber when engaged by the plunger of the injection device so as to cause the fluid in the chamber to be ejected from the pod through the needle 222.

At or near the leading end of the needle, the cartridge 204 may include an opening to allow the needle to extend therethrough to penetrate the skin of the user. For example, as shown in FIG. 10 a needle 222 may be housed within the cartridge 304 poised to extend through the opening. The cartridge may include a needle shroud 220 that secludes the needle unless/until the cartridge is pressed against the skin.

When the cartridge is pressed against the skin, the needle may approach the end of the opening or it may stay stationary until the hammer advances the needle into the skin. The injection component described above may be used to advance the needle to and into skin and the plunger may then be used to inject the fluid from the chamber.

In some embodiments, the injection device 202 or the cartridge 204 may have a needle depth setting or component. For example, the respective device may have a threaded component arranged on an end through which the needle may extend. The threaded component may be turned in one direction to lengthen the body of the injection device or cartridge, and in another direction to shorten the body of the injection device or cartridge. In this way, the threaded component may be configured to control a length of needle that extends from the injection device during an injection. Thus, the depth of the injection may be at least partially controlled by use of the threaded component. In other embodiments, the needle depth component may lengthen and shorten using different means, other than threading. In some embodiments, the needle depth component or setting may be adjustable by a user. In other embodiments, the needle depth component or setting may be a permanent or semi-permanent adjustment or setting, which may be pre-configured prior to the user's receipt of the kit. In some embodiments, a permanent, semi-permanent, or temporary needle depth setting may be configured such that a needle may extend no more than $\frac{1}{8}^{th}$ of an inch beyond the injection device, for example. In other embodiments, the needle depth setting may be configured for a longer or shorter needle depth.

Staging Template/Tray

As mentioned with respect to FIG. 3A/3B, a staging template 106 may be provided. The staging template 106 may be configured to hold the cartridges 104/204 in a position and/or arrangement for engagement by the injection device. The staging template 106 may come preloaded with cartridges in a sterilized, sealed package. In other embodiments, the staging template may be separate from the cartridges and the cartridges may be placed in the staging template by the user.

Figure 14:
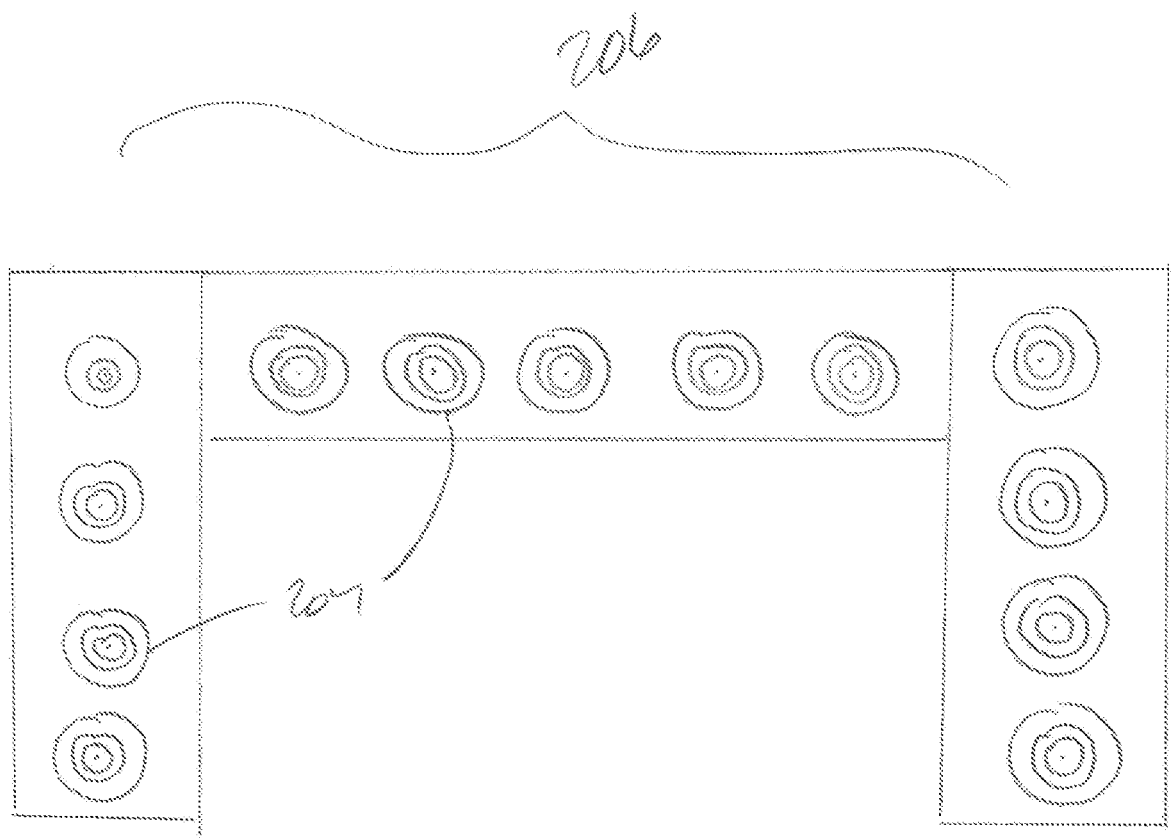
FIG. 14 is a top view of a staging tray holding a plurality of cartridges, according to one or more embodiments.

In some embodiments, as shown in FIG. 14, the staging template 206 may be arranged so as to correspond with the general arrangement and order of injections. For example, as shown, the staging template 206 may include a horseshoe or upside down U shape corresponding generally to the locations of injections extending upward/downward along the side of a left eye, across the top of the forehead, and upward/downward along the side of right eye. That is, as shown, the four left cartridges 204 may be used to perform four injections along the left eye. The five cartridges 204 arranged along the top may be used to perform injections across the forehead. The four right cartridges 204 may be used to perform four injections along the right eye. In one or more embodiments, the cartridges 204 arranged in the template 206 may have varying doses depending on the location of the corresponding injection. As such, the template 206 may be preloaded with the cartridges to assure proper doses are used in appropriate locations. In one or more embodiments, the staging template 206 shown in FIG. 14 may be assembled by the user. For example, while the cartridges may be preloaded into the template the template may be shipped in a plurality of parts as defined by the dividing lines. The template may be assembled by the user by place the template on a relatively flat counter top for example, and placing the pieces adjacent to each other as shown. In some embodiments, the template may include hook and loop, adhesive, or other fastening mechanisms to secure the several parts of the template together.

Patch/Injection Template

The injection patch may be adapted for particular placement on the body and may include injection locations configured to identify an injection site and/or guide placement of the injection device. In some embodiments, an adhesive may be arranged on a contact surface of the injection patch for adhering the patch to a user's skin and a numbing agent may be provided on the contact surface. In some embodiments, the injection patch may be sized and/or shaped for a particular body part. For example, an injection patch may be an eye patch 400 configured for one or more injections near a user's eye. Similarly, an injection patch may be a forehead patch 300, a neck patch, a scalp patch, or a combination thereof. In some embodiments, the cartridges in the kit may have varying quantities of botulinum toxin. In some embodiments, the injection locations and cartridges may be color-coordinated or otherwise identified, such that a user may select an appropriate cartridge with an appropriate amount of botulinum toxin for an appropriate injection location.

The holes 320/420 in the injection patch may be sized and configured to receive the leading end of the cartridges. In some embodiments, the shroud around the needle on the cartridge may have a shape and/or size matching that of the holes in the injection patch. As such, the placement of the injection device with a loaded cartridge may allow for the use of dexterity by the user to ascertain proper positioning of the injection device.

The injection patch may be composed of any suitable material(s) such as paper, plastic, fabric, and/or other suitable materials. The injection patch may generally have a contact surface or side configured to be arranged in contact with a user's skin. An adhesive component may be arranged on at least a portion of the contact surface. The adhesive component may include a relatively mild glue, for example. In some embodiments, the adhesive component may include a silicone-based adhesive, for example. The adhesive component may be arranged over all or a select portion of the contact surface of the patch.

In some embodiments, the injection patch may have a numbing agent arranged on at least a portion of the contact surface, so as to provide a numbing effect to help reduce pain at the injection site. The numbing agent may include lidocaine or a similar anesthetic component in some embodiments. The numbing agent may include, for example, between approximately 1% and 20% lidocaine in an aqueous base. Particularly, for example, the numbing agent may include approximately 5% lidocaine in an aqueous base in some embodiments. In some embodiments, the numbing agent may be combined with the adhesive element on the patch. In other embodiments, the numbing agent may be arranged over a portion of the contact surface of the patch, while the adhesive may be arranged over a different portion of the contact surface of the patch. In still other embodiments, the adhesive component may be arranged over the numbing agent, for example. In some embodiments, the numbing agent may begin to numb a user's skin upon contact.

In some embodiments, the injection patch may include a sponge-like material or other relatively flexible and/or porous material. The sponge-like material may be configured to absorb or retain a quantity of numbing agent. In some embodiments, the contact surface of the patch may include such material. For example, where the numbing agent is an aqueous lidocaine solution, the numbing agent may be arranged within the sponge-like material, and an adhesive may be arranged over the sponge-like material.

It may be appreciated that in some embodiments, an injection patch may have a buffer or a section of the patch that does not contain adhesive or numbing agent. For example, where a patch is configured to be arranged near a user's eye, the patch may have a buffer zone or component, such as a 2 millimeter zone or other appropriately sized zone, arranged nearest the user's eye, so as to mitigate seepage of the numbing agent and/or adhesive near the user's eye. In some embodiments, the buffer may include a portion of the sponge-like material described above.

In some embodiments, a covering, such as a paper or plastic based covering, may be arranged over the adhesive and/or numbing agent on the contact surface of the patch. The covering may be configured to protect the adhesive and/or numbing agent until use by a user. For example, the covering may be a peelable paper based liner.

Figure 15:
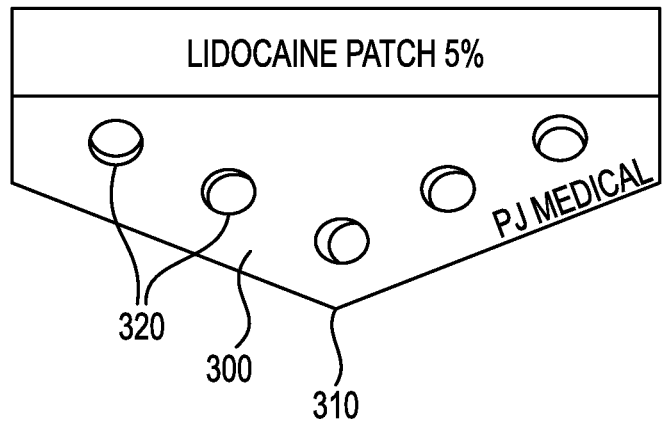
FIG. 15 is a front view of a forehead patch of the present disclosure, according to one or more embodiments.
Figure 16:
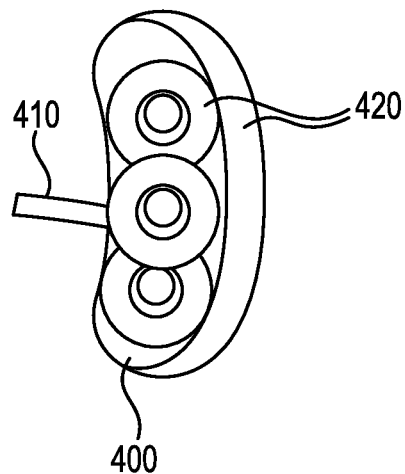
FIG. 16 is a front view of an eye patch of the present disclosure, according to one or more embodiments.

In some embodiments, one or more injection patches may be shaped, sized, and/or otherwise configured for use at a particular location on the user's body. For example, FIGS. 15 and 16 illustrate examples of a forehead patch 300 and an eye patch 400. Additionally, in some embodiments, the injection patch may have one or more openings 320/420, such that the user may position the syringe needle and inject the botulinum toxin solution through the patch. In this way, the one or more openings on the injection patch may operate as a guide to help users place the injections at the desired locations. As mentioned, the openings may be sized and shaped to receive the leading end of a cartridge, for example. In some embodiments, the injection patch may be partially or entirely transparent. For example, the injection patch may be transparent with the exception of colored rings around each injection opening.

Figure 17:
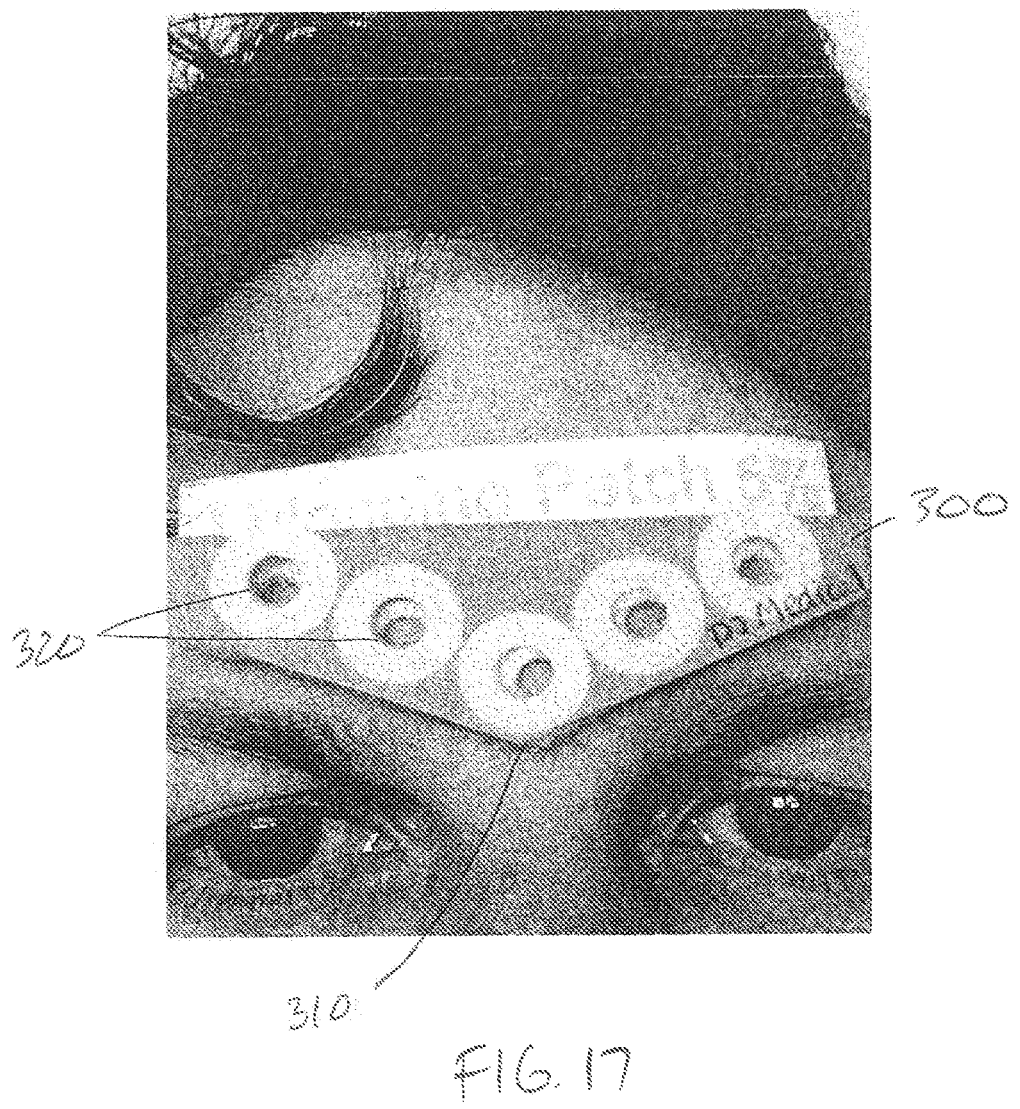
FIG. 17 is a front view of a forehead patch arranged on a user's forehead, according to one or more embodiments.

The forehead patch 300 may be configured to be arranged on a user's forehead area, generally above the nose and between the eyes, so as to target skin lines or wrinkles in this area. In some embodiments, the forehead patch may have one or more features to help a user position the patch in the desired location on the user's skin. For example, as shown in FIG. 15, the forehead patch 300 may have a registration feature 310, which may be, for example, a peak configured such that a user may position the peak centrally between the user's eyes and directed at the bridge of the nose. Additionally or alternatively, the forehead patch 300 may have one or more other registration features configured to help a user register the patch with respect to the user's forehead, hairline, eyes, nose, eyebrows, or other facial features. FIG. 17 shows the forehead patch 300 applied to a user's skin.

The forehead patch 300 may have one or more openings 320, as shown in FIG. 15. Each opening 320 may be arranged on the patch 300 so as to identify a desired location for an injection. For example, as shown in FIG. 15, in some embodiments, the forehead patch 300 may include 5 injection openings 320 configured to provide a guide for placing injections at 5 locations along the user's forehead. In other embodiments, the forehead patch 300 may include 1, 2, 3, 4, or any other suitable number of injection openings 120. Each opening 320 may generally be large enough for a user to arrange the syringe through the opening, and additionally may be small enough so as to identify a targeted location for the injection. In some embodiments, the openings 320 may be sized to receive the injection device. For example, the openings 320 may be configured such that a user may insert an injection end of the injection device through the opening in the patch. This may help ensure that the injection is placed centrally within the opening 320. The forehead patch 300 may generally be sized and shaped to accommodate the desired number of injection openings and to be arranged comfortably on the user's skin in the desired location. In one or more embodiments, the number of openings in the patch may correspond to the number of cells in the staging template holding the cartridges.

The eye patch 400 may be configured to be arranged near a user's eye area, such as alongside a user's eye, so as to target skin lines or wrinkles in this area. In some embodiments, the eye patch 400 may have one or more features to help a user position the patch in the desired location on the user's skin. For example, as shown in FIG. 16, the eye patch 400 may have a registration feature 410, such as for example a tab configured such that a user may position the tab proximate to the corner of the user's eye. As shown for example in FIG. 18, the registration feature 410 may be configured to be positioned at or near an outer corner of the user's eye, so as to position the eye patch 400 in a desired location. In some embodiments, the registration feature 410 may be removable, such that a user may use the tab to accurately position the patch 400, and then remove the tab for comfort and/or ease of injection. In other embodiments, the eye patch 400 may include additional or alternative registration features to help a user register the eye patch with respect to the user's eye, eyebrow, or other facial features.

Figure 18:
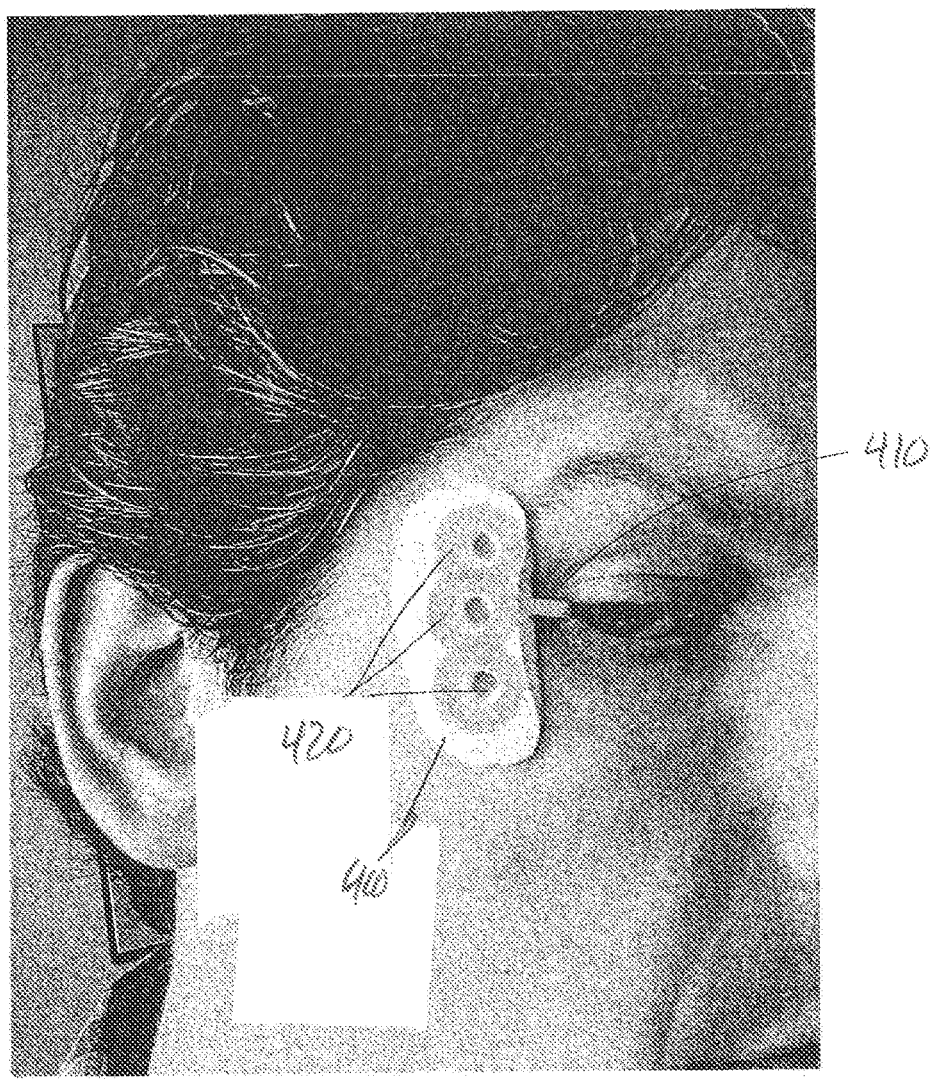
FIG. 18 is a front view of an eye patch arranged on a user's eye area, according to one or more embodiments.
Figure 19:
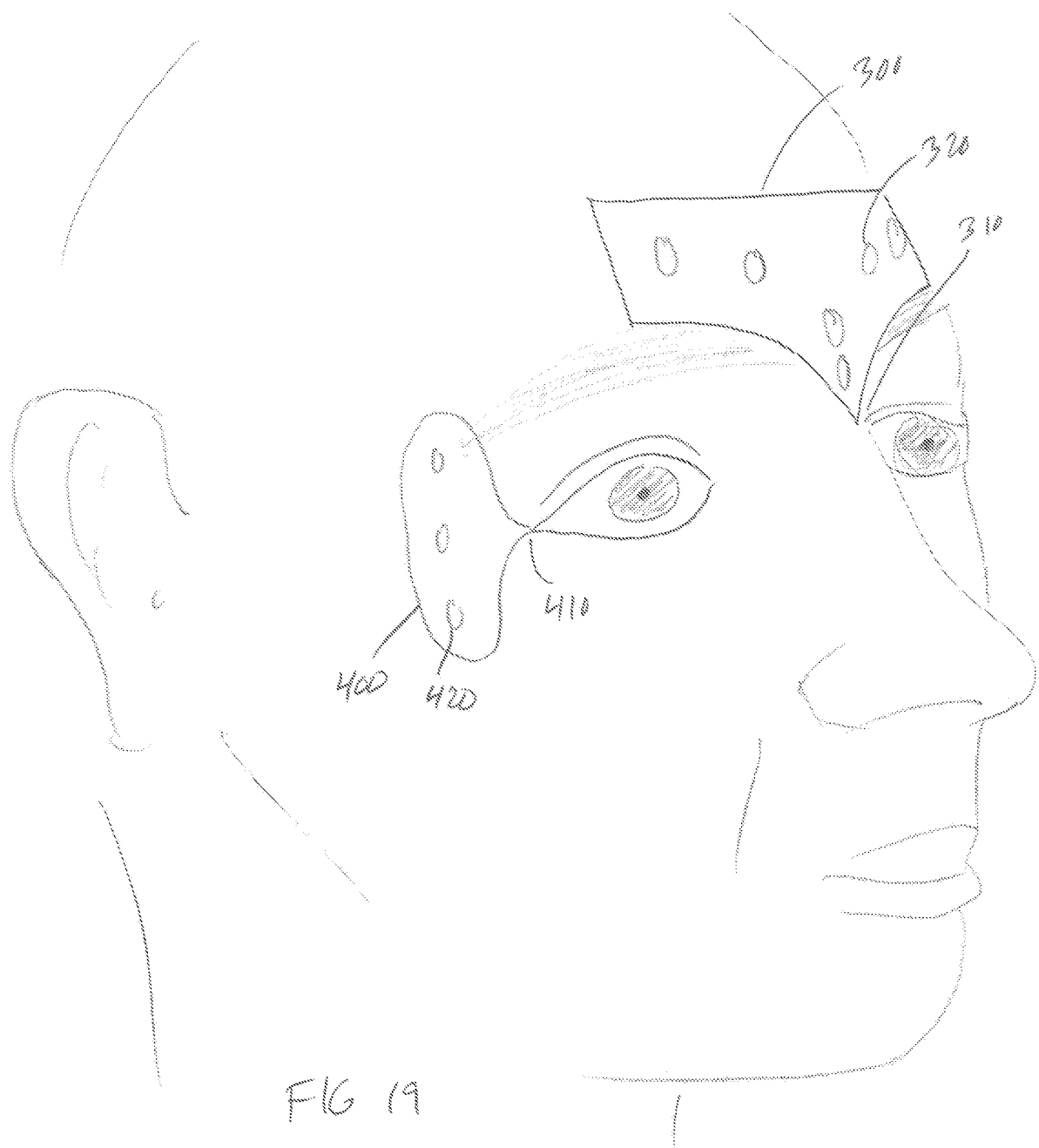
FIG. 19 is a perspective view of a user having a forehead patch and an eye patch in place, according to one or more embodiments.

The eye patch 400 may have one or more openings 420, as shown in FIGS. 16 and 18. Each opening 420 may be arranged on the patch 400 so as to identify a desired location for an injection. For example, as shown in FIGS. 16 and 18, in some embodiments, the eye patch 400 may include 3 injection openings 420 configured to provide a guide for placing injections at 3 locations near the user's eye. In other embodiments, the eye patch 400 may include 1, 2, 4, or any other suitable number of injection openings 420. Each opening 420 may generally be large enough for a user to arrange the syringe through the opening, and additionally may be small enough so as to identify a targeted location for the injection. In some embodiments, the openings 420 may be sized to receive the injection device. For example, the openings 420 may be configured such that a user may insert an injection end of the injection device through the opening in the patch 400. This may help ensure that the injection is placed centrally within the opening 420. The eye patch 400 may generally be sized and shaped to accommodate the desired number of injection openings 420 and to be arranged comfortably on the user's skin in the desired location. As with the forehead patch, in one or more embodiments, the number of openings in the patch 400 may correspond to the number of cells in the staging template holding the cartridges.

As mentioned, the one or more injection openings 320, 420 on each patch 300, 400 may be color coded or otherwise marked with an identifier. The color coding or other marking (s) of the injection openings may correspond with color coding or other identification of syringes or cartridges, as described above. That is, for example, where one or more cartridges or syringes are prefilled with quantities of botulinum toxin or botulinum toxin solution, the cartridges or syringes may have a color or other identifier to indicate the quantity of solution within the syringe. Such quantities may correspond with particular injection locations. For example, cartridges or syringes having 3 units of botulinum toxin or botulinum toxin solution may have a green cap, ring, sticker, or other component. Correspondingly, injection openings on the eye patch may be identified with a green circle or other component, or the eye patch itself may be green or have a green marker. Similarly, cartridges or syringes having 5 units of botulinum toxin or botulinum toxin solution may have a yellow cap, ring, sticker, or other component, and injection openings on the forehead patch may be identified with a yellow circle or other component. In some embodiments, an injection patch may have injection openings having different colors or other markings. For example, one patch may wrap around a the top and side of a user's eye and may have openings configured for forehead injections and eye injections. This use of corresponding colors or other matching identifiers between injection openings and cartridges or syringes may help a user to inject an appropriate amount of botulinum toxin or botulinum toxin solution at an appropriate location on the user's body. In other embodiments, other quantities and/or identifiers may be used.

While a particular type of system and kit have been described herein, still other approaches to self-administered botulinum toxin or other drugs, medicines, or solutions may be provided. The below discussion includes various other aspects of the system that may be in addition to or an alternative to the above described system.

In some embodiments, the kit may include a predetermined quantity of botulinum toxin. The toxin may be combined in a solution with one or more additional components, such as saline, in some embodiments. The botulinum toxin, saline, and/or other components may be combined in any suitable quantities and ratios. Where cartridges are not provided, for example, the botulinum toxin may be arranged in a bottle or vial, such as an injection vial having a rubberized opening configured to receive a syringe needle, or other container in some embodiments. In other embodiments, the botulinum toxin solution may be arranged within one or more syringes, as described below. In still other embodiments, the kit may exclude the botulinum toxin, such that a user may be required to obtain the solution from a medical professional or other source.

The syringes mentioned may be a standard plunger and barrel syringe having a hollow needle. In some embodiments, the syringe may have a standard barrel and/or needle size. In one or more embodiments, the syringe and/or the above-described cartridges may include a barrel size, or chamber size as the case may be, of 0.3 mL, 0.5 mL, or 1.0 mL. The barrel of the syringe or the chamber of the cartridge may have graduated 1-unit, 0.5-unit, 0.1 mL, or other suitable and/or standard interval. The needle in the syringe or the cartridge may have a gauge ranging between 28 and 31 gauge, and a length ranging between 4 mm and 12.7 mm (0.5 in) in some embodiments. In other embodiments, the syringe or cartridge may have any suitable and/or standard barrel size, needle gauge, and/or needle length. The syringe or cartridge may be sized and generally configured to inject a desired quantity of a botulinum toxin solution. For example, the syringe may be configured to measure and inject between approximately 1 and 10 units of a botulinum toxin solution. Particularly, the syringe or cartridge may be configured to measure and inject between 2 and 7.5 units of a botulinum toxin solution. More particularly, the syringe or cartridge may be configured to measure and inject between 3 and 5 units of a botulinum toxin solution in some embodiments. In other embodiments, the syringe or cartridge may be configured to measure and inject any other suitable quantity of a botulinum toxin solution or another suitable component.

The syringe or cartridge may be configured for single use and thus may be a disposable syringe or cartridge in some embodiments. In other embodiments, the syringe or cartridge may be reusable. In some embodiments, the kit may include a plurality of syringes or cartridges having one or more sizes. In some embodiments, the one or more syringes or cartridges may be pre-filled. That is, the kit may include one or more syringes or cartridges pre-filled with a desired quantity of botulinum toxin or botulinum toxin solution. Multiple syringes or cartridges may have varying quantities of botulinum toxin or solution in some embodiments. For example, some syringes or cartridges may be pre-filled with 3 units of the toxin or solution, while other units may be pre-filled with 5 units of the toxin or solution.

In one or more embodiments, where for example a syringe is supplied in lieu of a cartridge, the syringe may have one or more safety features. For example, the syringe may have a safety cap covering the needle end of the syringe and/or the plunger end of the syringe (i.e. preventing the plunger from being pulled or pushed). The syringe may additionally have a tamper proof tape and/or other safety features. In some embodiments, the syringe may have one or more features configured to increase difficulty of using the syringe without an injection device. That is, the syringe may be configured to discourage users from simply pressing the plunger down with a hand or finger to inject manually. For example, the syringe may be configured such that it may be generally difficult to grasp or hold manually for injection. Where a user may otherwise place his or her fingers or thumb to push or pull the plunger manually, the syringe may have one or more cone-shaped elements or other relatively pointed or sharp elements configured to discourage finger placement. Additionally or alternatively, the syringe may have one or more features configured for use with an injection device, such as those devices discussed herein. In some embodiments, the syringe may be pre-loaded into a cartridge configured for use with an injection device, as described above. It is to be appreciated that while the above safety features have been described with respect to a syringe, the same or similar safety features may be applicable to a cartridge. For example, either a syringe or a cartridge may benefit from a safety cap. Still further, the primary difference between the syringe and the cartridge may be the absence of a plunger on the cartridge. That is, the cartridge was described as having a chamber with a plug that moves through the chamber to eject the solution and the plunger for advancing the plug may be present on the injection device. As such, the cartridge might not include a plunger. However, as shown in FIG. 10, the trailing end of the plug includes a shaft-like element that may be referred to as a plunger.

In some embodiments, one or more cartridges or syringes may be particularly identified for a use. Particularly, cartridges or syringes having differing sizes and/or filled with differing botulinum toxin or botulinum toxin solution quantities may be color-coded or otherwise coded or marked to identify their suitability for different uses. For example, syringes or cartridges having 3 units of botulinum toxin or botulinum toxin solution may be color-coded or otherwise coded or marked to identify their suitability for use around a user's eyes or eyelids, and syringes or cartridges having 5 units of botulinum toxin or botulinum toxin solution may be color-coded or otherwise coded or marked to identify their suitability for use around a user's forehead area. In one embodiment, syringes or cartridges may have a colored needle cap, plunger end cap, wrapper, ring, sticker, or other component for identification.

In some embodiments, the kit may include an injection device configured to assist with injection of the botulinum toxin. In some embodiments, the injection device may be an automatic injection device, such as an AUTOJECT device, configured to receive a standard syringe and automatically push the plunger of the syringe to inject the botulinum toxin into the user's muscle or other tissue. In some embodiments, the injection device may be configured to receive a particular syringe size. In this way, the injection device may have an inner width or diameter configured to minimize movement of the syringe within the device. In some embodiments, the injection device may have a ballpoint pen-like design. The injection device may have one or more ergonomic features in some embodiments. The injection device may be a reloadable device, such that the user may perform multiple injections with the device. In other embodiments, the injection device may be a single-use device having, for example, a pre-loaded syringe component. In some embodiments, the injection device may be a spring activated device. For example, a syringe may be loaded within the injection device against a compressed or partially compressed spring. The spring may operate to push the plunger of the syringe so as to expel the botulinum toxin through the needle of the syringe.

The injection device may generally be configured to help a user to safely and effectively deliver an injection of botulinum toxin or another component without, for example, injecting the needle too deep beneath the user's skin. For example, where a user may be injecting botulinum toxin around the eye area, the injection device may help to ensure that the user does not inject the needle too deep around the eyeball or eye socket. The injection device may help to control the direction and angle of the injection. Moreover, the injection device may, in some embodiments, conceal or partially conceal the syringe and/or needle before and/or during an injection. In this way, the injection device may help calm users who may have needle phobias or other difficulties with needles or syringes.

A botulinum toxin self-administration kit or system may be available to a user for at-home use in some embodiments. In other embodiments, such a kit or system may be available to a physician, nurse, or other medical professional for in-clinic or other in-office use, for example. In some embodiments, the kit may be configured for a particular use. For example, some kits may be configured for use with particular areas of the body, such as the eye area, forehead area, neck, scalp, or a combination thereof. In this way, a kit may have one or more patches and one or more syringes, injection devices, and/or botulinum toxin quantities configured for use on the particular area of the body. Other kits may include patches, syringes, injection devices, and/or botulinum toxin quantities for multiple body areas. In some embodiments, kits may have other selectable or variable components or features. For example, some kits may have relatively higher or lower botulinum toxin quantities, number of injections, or patch sizes.

In some embodiments, the present disclosure relates to a method for self-administering a botulinum toxin injection. The method may include requesting a self-administered botulinum toxin kit, selecting an injection patch, positioning the injection patch on the body, selecting a cartridge, engaging the cartridge with the injection device, and injecting the botulinum toxin.

In some embodiments, requesting a self-administered botulinum toxin kit may include obtaining a prescription or medical professional recommendation for botulinum toxin injections. The kit may be requested by a user or the user's medical professional in some embodiments. The kit may be requested by any suitable means, such as through a website, application, email, mail, telephone call, or any other suitable means. As described above, in some embodiments, botulinum toxin kits may be configured for different types of uses or injections. In this way, a user may request a kit particular to the user's needs.

The method for self-administered botulinum toxin injection may additionally include selecting an injection patch. As described above, some injection patches may be configured for particular injection areas or areas of the body. For example, where a user desires to inject botulinum toxin around the user's eye area(s) to target lines or wrinkles around the eye area, the user may select an injection patch particularly configured for the eye area.

The user may position the injection patch on the body area that will receive one or more injections. In some embodiments, the user may remove a covering, such as a protective covering over a contact side of the patch, before positioning the patch. Moreover, as described above, positioning the patch may include registering the injection patch with a body part or feature. For example, the user may align a registration tab, peak, or other element with the user's eye, nose, brow, or other body part or facial feature. In some embodiments, the user may optionally remove the registration tab or other registration element after positioning the injection patch.

The user may select a cartridge for injecting the botulinum toxin. In some embodiments, this may include selecting a prefilled cartridge from a staging tray, based on a desired quantity of botulinum toxin or botulinum toxin solution or a location to be injected. For example, as described above, the user may select a syringe having a color or other identifier matching that of a corresponding injection hole and/or patch color or identifier. In other embodiments, the user may select a cartridge based on size or other factors such as its location in the staging tray that corresponds to a location of an injection. In some embodiments, where a prefilled cartridge is not used, the user may draw a desired quantity of botulinum toxin or solution into the syringe.

In some embodiments, the user may engage a cartridge with the injection device by pressing the injection device onto the selected cartridge in the staging tray. The engagement of the cartridge in the tray may naturally cock the hammer and ready the injection device for injection. In one or more other embodiments, the user may arrange the selected syringe in an injection device. This may include loading the injection device with the syringe, and cocking the injection device as described above, or otherwise readying the injection device for injection. In some embodiments, as described above, the injection device may be pre-loaded with a syringe, and the user may select an appropriate injection device and ready the injection device for injection.

The user may use the injection device with the cartridge or syringe to inject the botulinum toxin into the user's muscle or other tissue at the desired injection site. This may include positioning the syringe and/or injection device through an injection opening in the patch, pressing the injection device against the skin to release a safety mechanism, and pressing the trigger of the injection device causing the injection device to advance the needle into the skin followed by injection of the botulinum toxin or other solution.

FIG. 20 shows one embodiment of a workflow method of the present disclosure. As shown, the method may include a doctor prescribing a botulinum toxin injection kit, or a user otherwise ordering or purchasing a botulinum toxin injection kit. The method may include activation of the botulinum toxin by a manufacturer, who may then ship the kit. The kit may be received at a treatment location, and the botulinum toxin may be refrigerated until use. A user of the kit may prepare for injection by inserting a cartridge into the injection device or engaging a cartridge with the injection device, for example, or otherwise preparing cartridge and/or syringe for use. The user may apply a numbing agent to the injection site. As indicated above, the numbing agent may be arranged on an injection patch in some embodiments. The user may apply an injection patch, or injection map, to the injection site. The user may cock the injection device by, for example, pulling back or setting a hammer of the device. This may also occur by engagement of the cartridge. A user may load a first cartridge, remove a safety cap and/or foil seal on the cartridge, arrange the injection device at a first injection site according to the injection patch or map, compress a safety mechanism of the injection device, and cause the hammer to release thus injecting the botulinum toxin. A user may then reset the hammer or otherwise reset the injection device, and may remove and/or dispose of the cartridge, syringe, and/or needle. In some embodiments, a next cartridge may be loaded into the device to perform a next injection. Also, rather than resetting the injection device, this may occur naturally by engaging a second cartridge in the staging tray. After all injections are completed, the user may remove the injection patch or map, dispose of used disposable portions of the kit, and/or clean the injection device.

Figure 21:
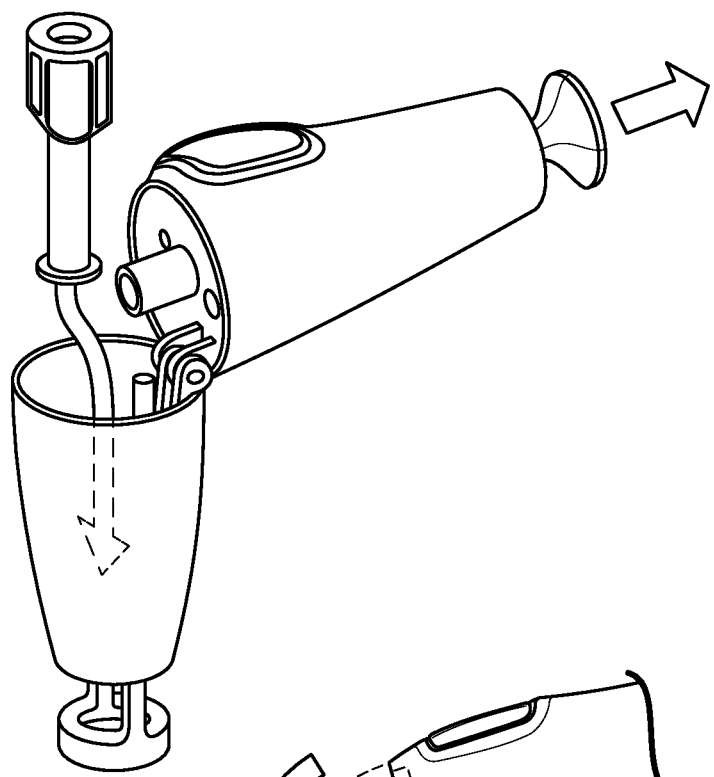
FIG. 21 is a perspective view of an injection device of the present disclosure, according to one or more embodiments.
Figure 22:
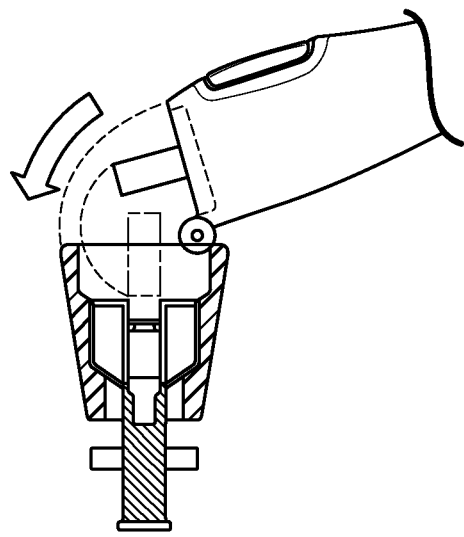
FIG. 22 is a side view thereof.

FIGS. 21-31 show additional examples of injector devices of the present disclosure, and some methods of using and/or operating such devices. For example, FIGS. 21 and 22 shows two views of an injector device having a hinged handle portion to facilitate insertion of a cartridge portion. As shown, the handle portion may be openable or separable into two portions at the hinge, such that a cartridge may be inserted or loaded into the handle portion to prepare for an injection. The handle portion may be closed after insertion of the cartridge portion. The handle portion may have a compressible safety mechanism configured to enclose around a needle until compressed prior to or during injection. The handle portion may have an injection button configured to cause a hammer to depress a plunger, thus, causing an injection. The handle portion may additionally have a reset mechanism, such as a pull mechanism, configured to reset, or pull back, the hammer after an injection.

Figure 23:
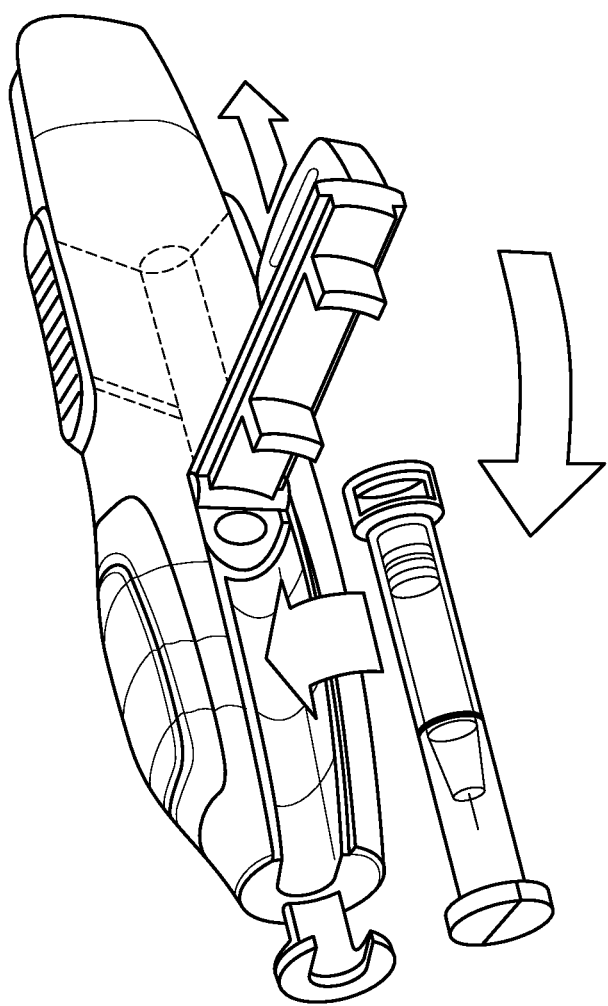
FIG. 23 is a perspective view of an injection device of the present disclosure, according to one or more embodiments.

FIG. 23 shows another embodiment of an injector device of the present disclosure. As shown, the injector device may have a handle portion with a hinged door openable such that the handle portion may receive a cartridge portion. The cartridge portion may be inserted or loaded into the handle portion, and the hinged door may be closed. The handle portion may be closed after insertion of the cartridge portion. The handle portion may have a compressible safety mechanism configured to enclose around a needle until compressed prior to or during injection. The handle portion may have an injection button configured to cause a hammer to depress a plunger, thus causing an injection. The handle portion may additionally have a reset mechanism, such as a slide mechanism, configured to reset, or pull back, the hammer after an injection.

Figure 24:
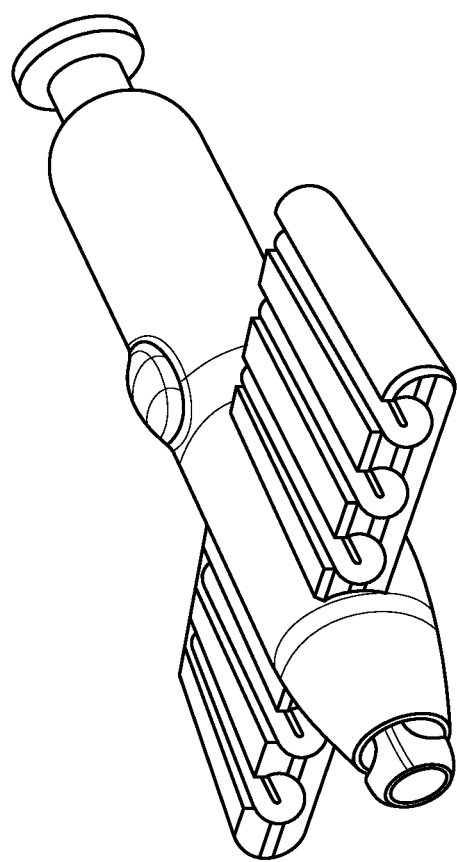
FIG. 24 is a perspective view of an injection device of the present disclosure, according to one or more embodiments.

FIG. 24 shows another embodiment of an injector device of the present disclosure. As shown, the injector device may have a handle portion with an opening configured to receive a cartridge array. The cartridge array may hold a plurality of cartridges, and may be configured to move through the handle portion to align each of the plurality of cartridges within the handle portion for injection. The handle portion may have a compressible safety mechanism configured to enclose around a needle until compressed prior to or during injection. The handle portion may have an injection button configured to cause a hammer to depress a plunger of an aligned cartridge, thus causing an injection. The handle portion may additionally have a reset mechanism, such as a pull mechanism, configured to reset, or pull back, the hammer after an injection.

Figure 26:
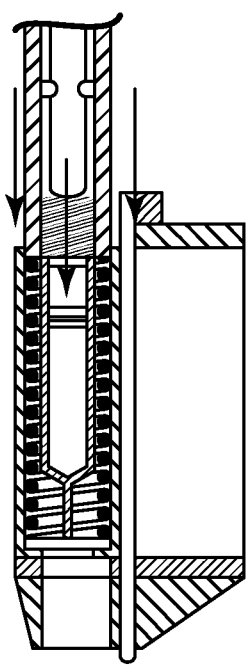
FIG. 26 is a cross-sectional side view thereof.
Figure 25:
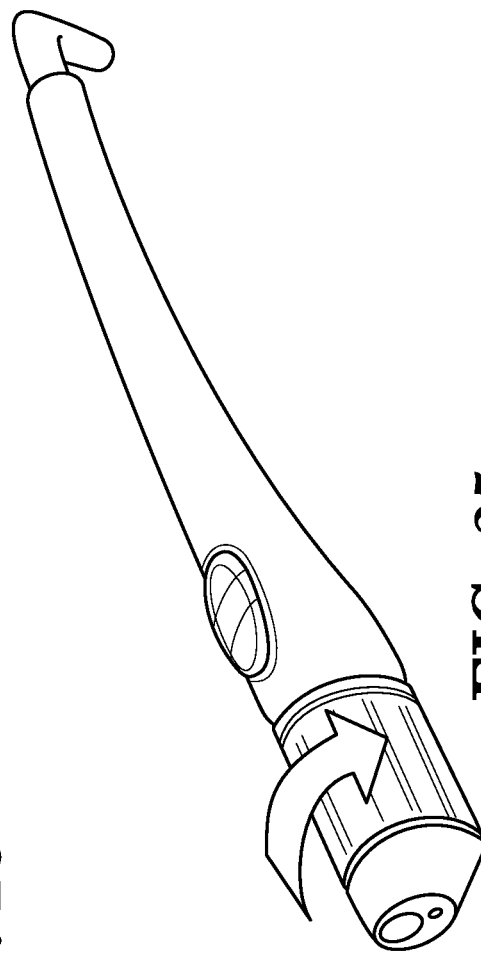
FIG. 25 is a perspective view of an injection device of the present disclosure, according to one or more embodiments.
Figure 27:
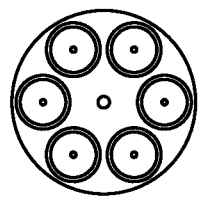
FIG. 27 is a cross-sectional end view thereof.

FIGS. 25-27 show another embodiment of an injector device of the present disclosure. As shown, the injector device may have a cartridge portion holding a plurality of syringes. The cartridge portion may be arranged on or in connection with a handle portion. The cartridge portion may have a rounded or circular cross sectional shape and the plurality of syringes may be evenly arranged, and in a circular pattern in some embodiments. The cartridge portion may be configured to rotate to align each of the plurality of syringes with the handle portion, or with a hammer within the handle portion, for injection. The handle portion may have a compressible safety mechanism configured to extend proximate to a needle until compressed prior to or during injection. The handle portion may have an injection button configured to cause a hammer to depress a plunger of an aligned syringe in the cartridge portion, thus causing an injection. The handle portion may additionally have a reset mechanism, such as a pull mechanism, configured to reset, or pull back, the hammer after an injection.

Figure 28:
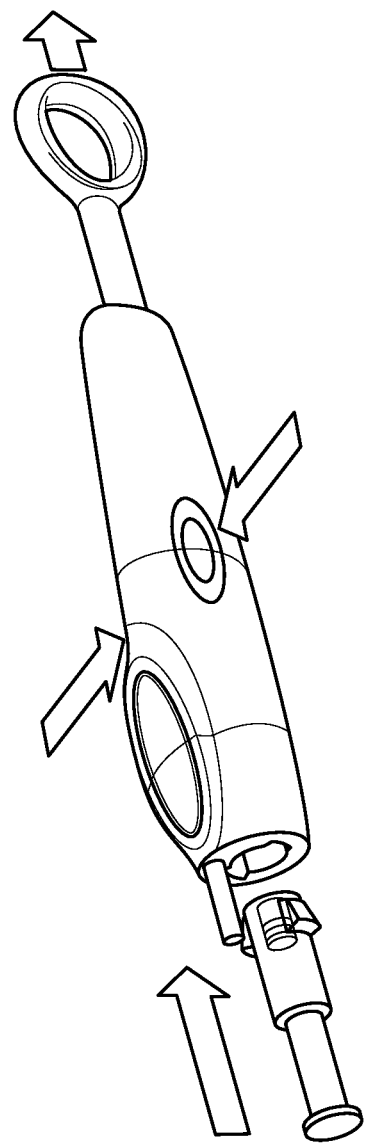
FIG. 28 is a perspective view of an injection device of the present disclosure, according to one or more embodiments.

FIG. 28 shows another embodiment of an injector device of the present disclosure. As shown, the injector device may have an end opening configured to receive a cartridge portion. The cartridge portion may be inserted into the opening of the handle portion prior to an injection. The handle portion may have a compressible safety mechanism configured to extend proximate to a needle until compressed prior to or during injection. The handle portion may have an injection button configured to cause a hammer to depress a plunger of the syringe in the cartridge portion, thus causing an injection. The handle portion may additionally have a reset mechanism, such as a pull mechanism, configured to reset, or pull back, the hammer after an injection. The handle portion may have a cartridge release mechanism, such as a pair of cartridge release buttons, configured to release the cartridge portion from the handle portion.

Figure 29:
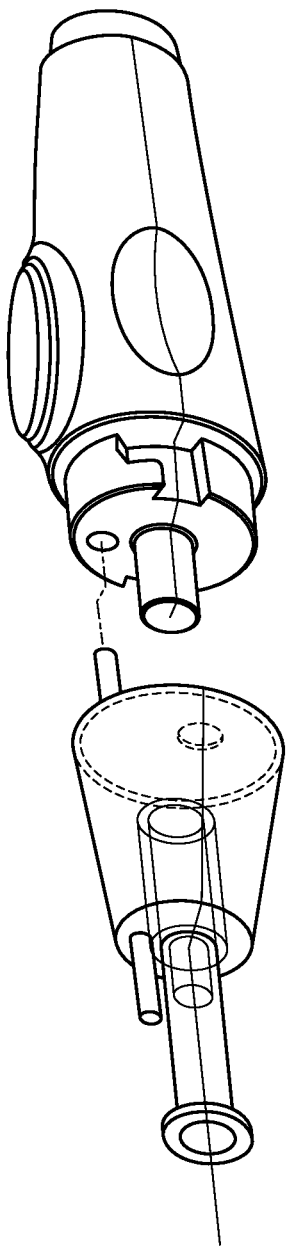
FIG. 29 is a perspective exploded view of an injection device of the present disclosure, according to one or more embodiments.
Figure 30:
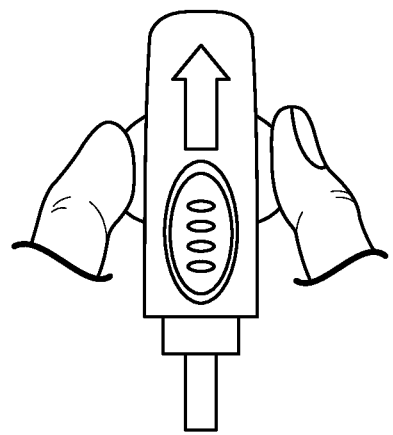
FIG. 30 is a side view thereof.
Figure 31:
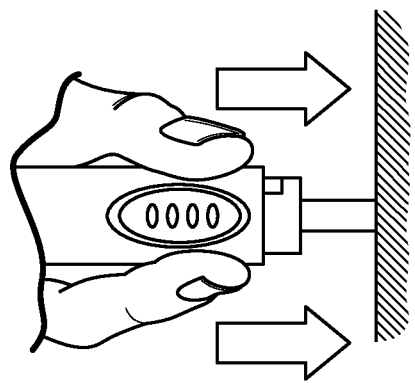
FIG. 31 is an additional side view thereof.
Figure 35:
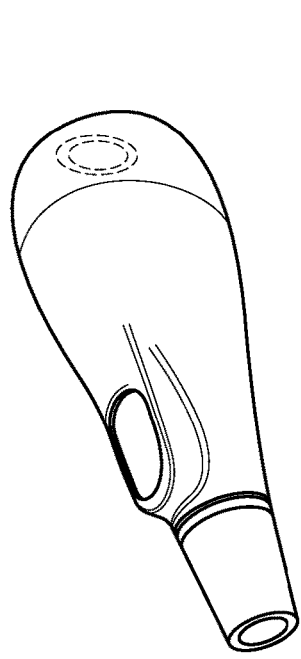
FIG. 35 is a perspective view of an injection device of the present disclosure, according to one or more embodiments.
Figure 36:
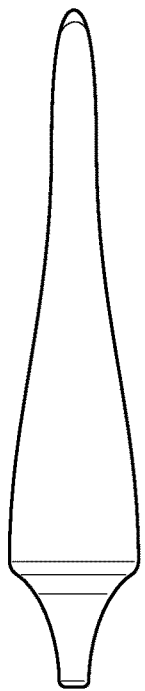
FIG. 36 is a perspective view of an injection device of the present disclosure, according to one or more embodiments.
Figure 37:
FIG. 37 is a perspective view of an injection device of the present disclosure, according to one or more embodiments.
Figure 38:
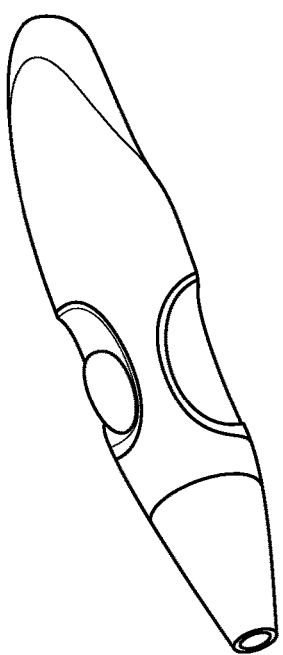
FIG. 38 is a perspective view of an injection device of the present disclosure, according to one or more embodiments.
Figure 32:
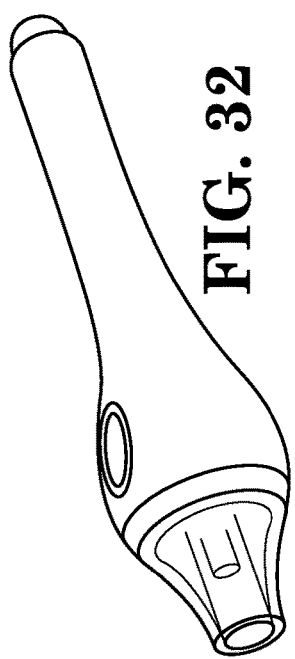
FIG. 32 is a perspective view of an injection device of the present disclosure, according to one or more embodiments.
Figure 33:
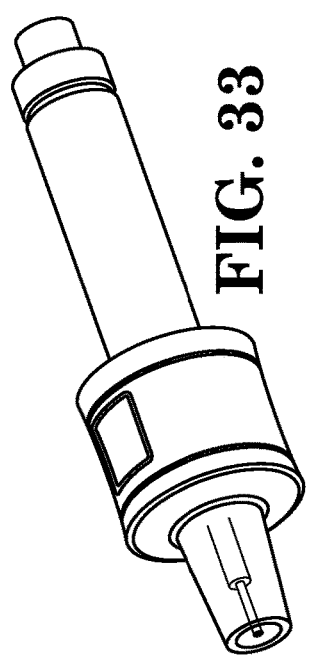
FIG. 33 is a perspective view of an injection device of the present disclosure, according to one or more embodiments.
Figure 34:
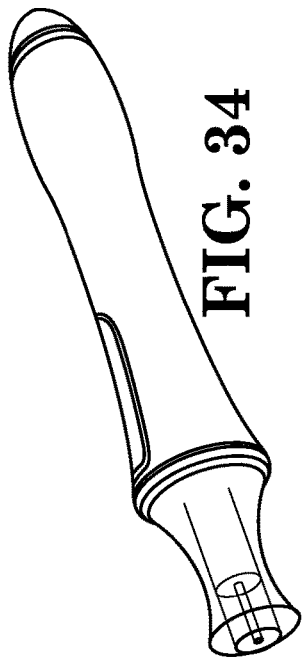
FIG. 34 is a perspective view of an injection device of the present disclosure, according to one or more embodiments.
Figure 42:
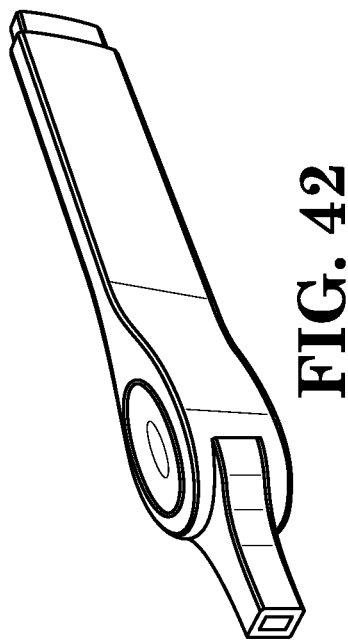
FIG. 42 is a perspective view of an injection device of the present disclosure, according to one or more embodiments.
Figure 43:
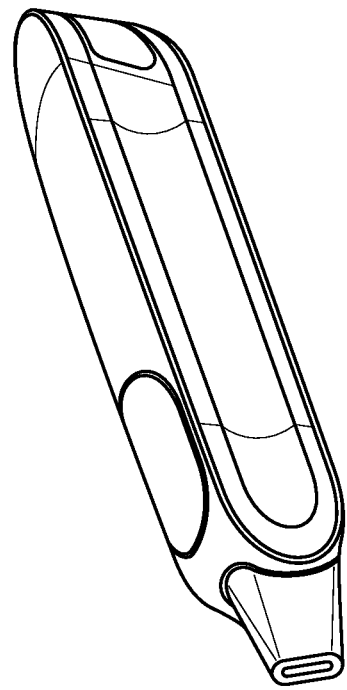
FIG. 43 is a perspective view of an injection device of the present disclosure, according to one or more embodiments.
Figure 39:
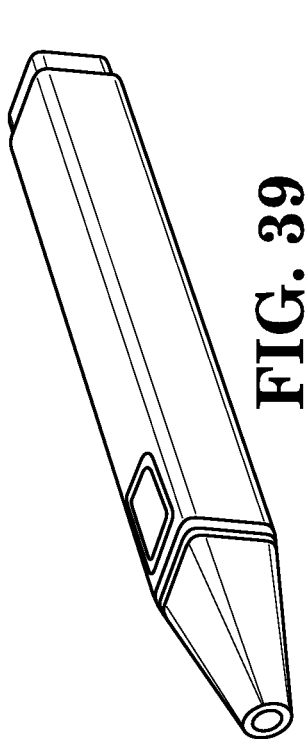
FIG. 39 is a perspective view of an injection device of the present disclosure, according to one or more embodiments.
Figure 40:
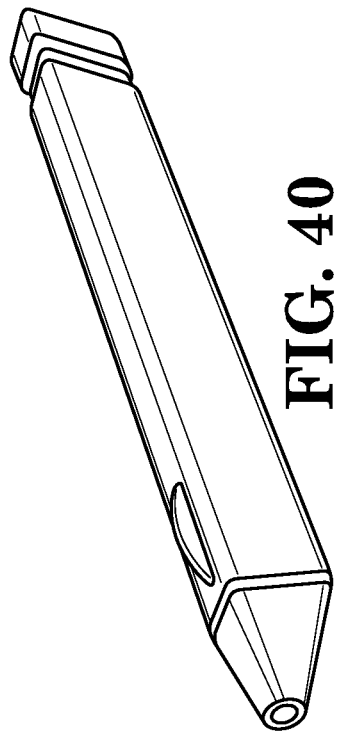
FIG. 40 is a perspective view of an injection device of the present disclosure, according to one or more embodiments.
Figure 41:
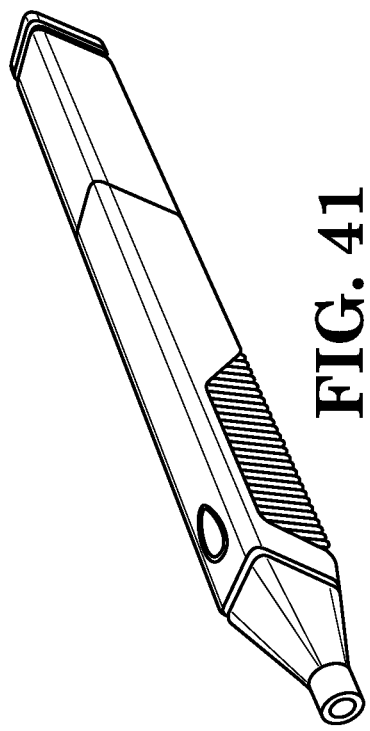
FIG. 41 is a perspective view of an injection device of the present disclosure, according to one or more embodiments.
Figure 44:
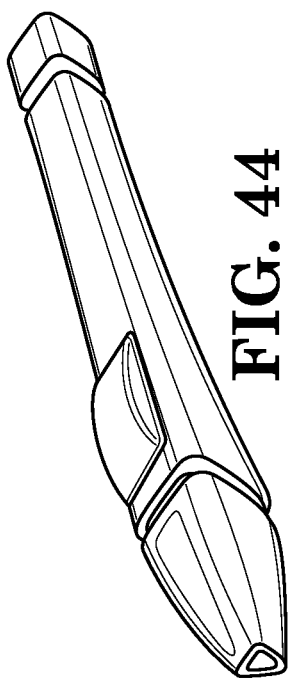
FIG. 44 is a perspective view of an injection device of the present disclosure, according to one or more embodiments.
Figure 45:
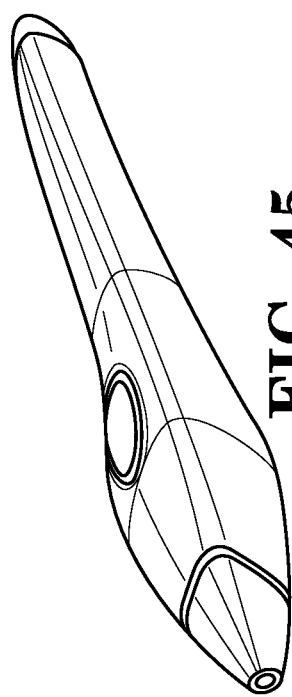
FIG. 45 is a perspective view of an injection device of the present disclosure, according to one or more embodiments.
Figure 46:
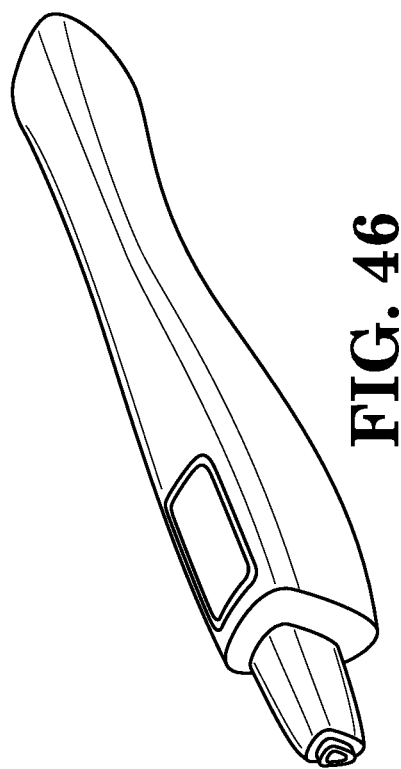
FIG. 46 is a perspective view of an injection device of the present disclosure, according to one or more embodiments.
Figure 47:
FIG. 47 is a perspective view of an injection device of the present disclosure, according to one or more embodiments.
Figure 48:
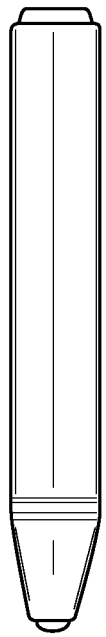
FIG. 48 is a perspective view of an injection device of the present disclosure, according to one or more embodiments.
Figure 49:
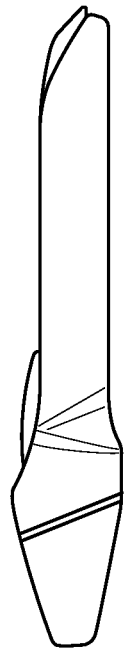
FIG. 49 is a perspective view of an injection device of the present disclosure, according to one or more embodiments.
Figure 53:
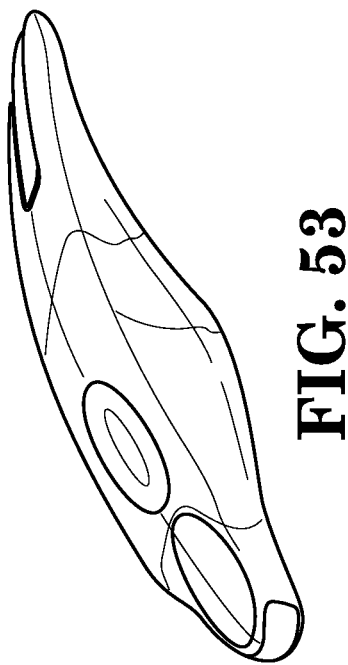
FIG. 53 is a perspective view of an injection device of the present disclosure, according to one or more embodiments.
Figure 54:
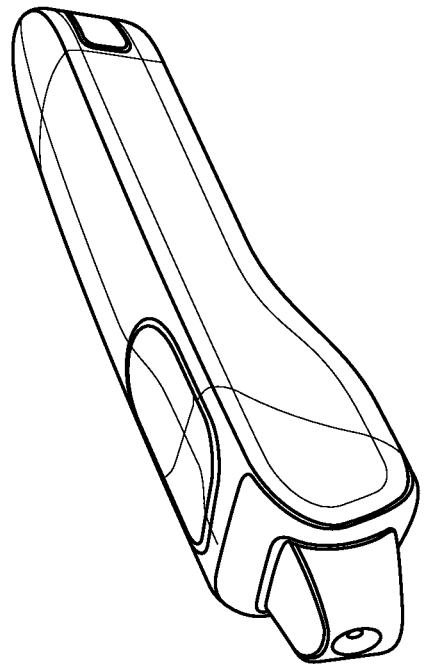
FIG. 54 is a perspective view of an injection device of the present disclosure, according to one or more embodiments.
Figure 50:
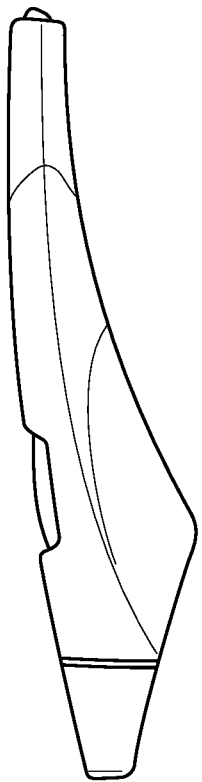
FIG. 50 is a perspective view of an injection device of the present disclosure, according to one or more embodiments.
Figure 51:
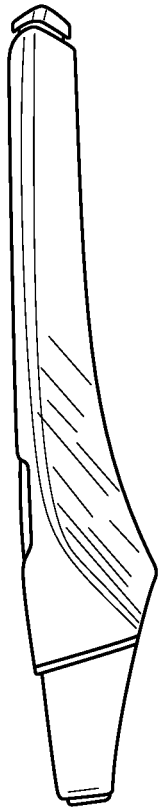
FIG. 51 is a perspective view of an injection device of the present disclosure, according to one or more embodiments.
Figure 52:
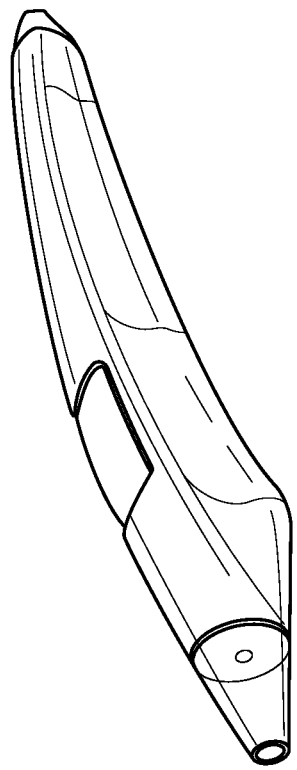
FIG. 52 is a perspective view of an injection device of the present disclosure, according to one or more embodiments.
Figure 58:
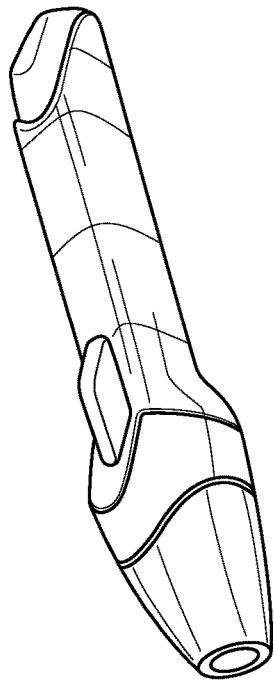
FIG. 58 is a perspective view of an injection device of the present disclosure, according to one or more embodiments.
Figure 59:
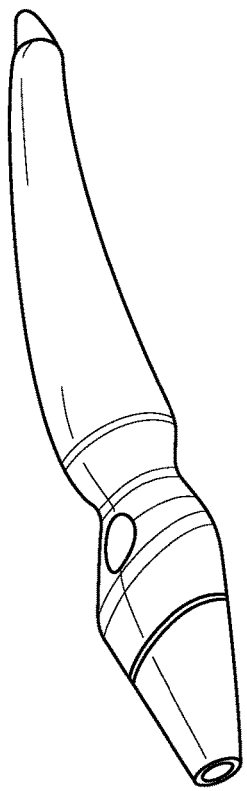
FIG. 59 is a perspective view of an injection device of the present disclosure, according to one or more embodiments.
Figure 60:
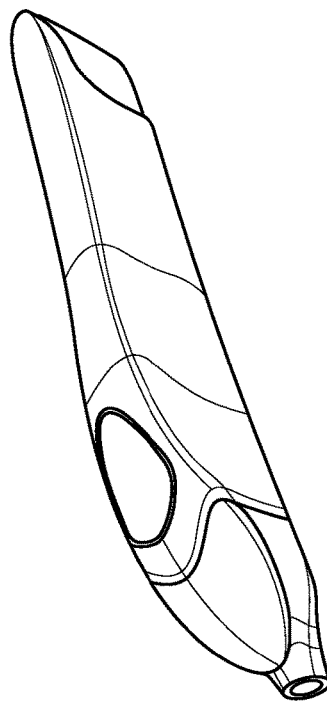
FIG. 60 is a perspective view of an injection device of the present disclosure, according to one or more embodiments.
Figure 55:
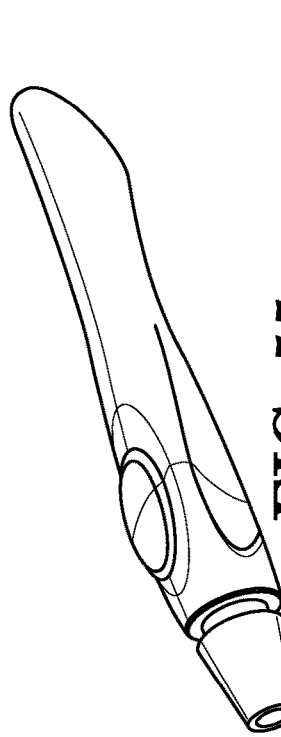
FIG. 55 is a perspective view of an injection device of the present disclosure, according to one or more embodiments.
Figure 56A:
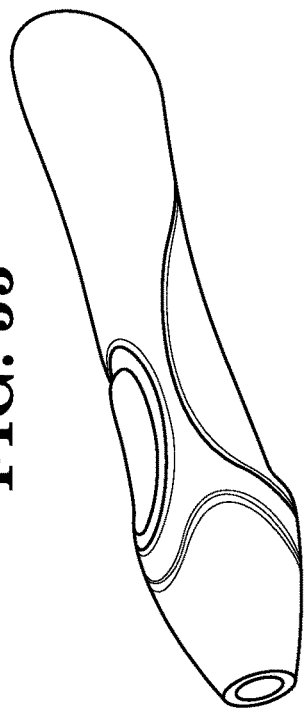
FIG. 56A is a perspective view of an injection device of the present disclosure, according to one or more embodiments.
Figure 56B:
FIG. 56B is a side view thereof.
Figure 57:
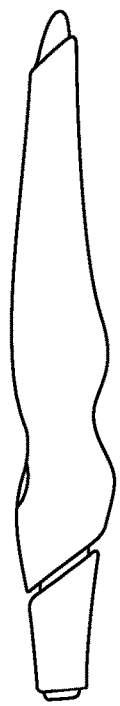
FIG. 57 is a perspective view of an injection device of the present disclosure, according to one or more embodiments.

FIGS. 29-31 shows another embodiment of an injector device of the present disclosure. As shown, the injection device may have a handle portion configured to receive a cartridge portion. For example, the handle portion may have one or more slots or grooves configured to align with corresponding tabs of the cartridge portion. In some embodiments, a hammer, configured to align with a plunger of a syringe, may extend from the handle portion. The hammer may be configured to be set or cocked, such that a user may push the hammer back such as by pressing it against a surface, prior to loading a cartridge onto the handle portion. The cartridge portion may hold a needle and may have a compressible safety mechanism configured to extend proximate to a needle until compressed prior to or during injection. The handle portion may have an injection button configured to cause the hammer to depress the plunger of the syringe in the cartridge portion, thus causing an injection. The handle portion may have a cartridge release mechanism, such as a pair of cartridge release buttons, configured to release the cartridge portion from the handle portion.

FIGS. 32-60 show some additional embodiments of injection devices of the present disclosure, each with a handle portion and a cartridge portion. As shown, injection devices may have variety of different shapes and designs. The handle portion may have a variety of ergonomic features, as shown. Moreover, the injection devices may have a plurality of aesthetic features as well.

It is to be appreciated that, while a variety of embodiments have been described herein, the various features from the different embodiments may be combined. For example, features from a first injection device, as described herein, may be combinable with features of a second injection device described herein.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A method of self-administering an injection of solution, the method comprising:
  positioning an injection patch on a particular body part, the injection patch being configured to indicate a location of each of a plurality of injection sites, wherein the injection patch is shaped for the body part and includes a plurality of location indicators, each of the plurality of location indicators correlating with one of the plurality of injection sites on the body part, wherein the injection patch includes an adhesive on a contact surface thereof for adhering the injection patch to the body part, and wherein positioning the injection patch includes aligning each of the plurality of location indicators with the correlating injection site on the body part such that the injection patch provides a guide for placing injections at the plurality of injection sites on the particular body part;
  adhering the injection patch to the contact surface;
  engaging a first cartridge with an injection device to select the first cartridge from one of a plurality of cartridges in a tray, the first cartridge containing the solution;
  aligning the injection device and the first cartridge with a first location indicator of the plurality of location indicators on the injection patch;
  pressing the injection device against the body part, thereby releasing a safety mechanism;
  depressing a trigger on the injection device and thereby inserting a needle of the first cartridge through the injection patch at the first location indicator and injecting the solution;
  engaging a second cartridge with the injection device to select the second cartridge from one of the plurality of cartridges in the tray, the second cartridge containing the solution;
  aligning the injection device and the second cartridge with a a second location indicator of the plurality of location indicators on the injection patch;
  pressing the injection device against the body thereby releasing the safety mechanism; and
  depressing the trigger on the injection device and thereby inserting a needle of the second cartridge through the injection patch at the second location indicator and injecting the solution.

2. The method of claim 1, wherein the tray is a staging tray.

3. The method of claim 2, wherein the staging tray includes the plurality of cartridges arranged in locations corresponding to the injection sites.

4. The method of claim 1, wherein aligning the injection device and the first cartridge comprises placing a tip of the first cartridge in an opening in the injection patch, wherein the opening corresponds to one of the plurality of location indicators on the injection patch.

5. The method of claim 1, wherein each location indicator corresponds to a specific cartridge.

6. The method of claim 1, wherein the injection patch includes a registration feature configured for positioning at a feature on the body part so as to position the injection patch in a desired location, wherein positioning the injection patch comprises positioning the registration feature at the feature on the body part.

7. The method of claim 1, wherein the injection patch includes a numbing agent provided on a portion of the contact surface.

8. The method of claim 7, wherein the injection patch includes a sponge-like material configured to retain a quantity of the numbing agent.

9. The method of claim 1, wherein the plurality of cartridges are color coordinated with the plurality of location indicators such that each cartridge corresponds to an associated location indicator, the method further comprising a user selecting an appropriate cartridge from the tray based on the color coordination.

10. The method of claim 1, wherein pressing the injection device against the body part causes the cartridge to come into contact with a body portion of the injection device and thereby release the safety mechanism.

11. The method of claim 1, wherein the injection patch is shaped as one of a forehead patch or an eye patch.

12. A method of self-administering an injection of solution, the method comprising:
  positioning an injection patch on a particular body part, the injection patch being configured to indicate a location of a plurality of injection sites, wherein the injection patch is shaped for the body part and includes a plurality of location indicators, each of the plurality of location indicators correlating with one of the plurality of injection sites on the body part, wherein positioning the injection patch includes aligning each of the plurality of location indicators with the correlating injection site on the body part such that the injection patch provides a guide for placing injections at the plurality of injection sites on the particular body part;

engaging a first cartridge with an injection device to select the first cartridge from one of a plurality of cartridges in a tray, the first cartridge containing the solution, wherein engaging the first cartridge with the injection device comprises pressing down on the first cartridge with the injection device;

aligning the injection device and the first cartridge with a first location indicator of the plurality of location indicators on the injection patch;

pressing the injection device against the body part, thereby releasing a safety mechanism;

depressing a trigger on the injection device and thereby inserting a needle of the first cartridge through the injection patch at the first location indicator and injecting the solution;

engaging a second cartridge with the injection device to select the second cartridge from one of the plurality of cartridges in the tray, the second cartridge containing the solution;

aligning the injection device and the second cartridge with a second location indicator of the plurality of location indicator on the injection patch;

pressing the injection device against the body thereby releasing the safety mechanism; and depressing the trigger on the injection device and thereby inserting a needle of the second cartridge through the injection patch at the second location indicator and injecting the solution.

13. A method of self-administering an injection of solution, the method comprising:

positioning an injection patch on a particular body part, the injection patch being configured to indicate a location of a plurality of injection sites, wherein the injection patch is shaped for the body part and includes a plurality of location indicators, each of the plurality of location indicators correlating with one of the plurality of injection sites on the body part, wherein positioning the injection patch includes aligning each of the plurality of location indicators with the correlating injection site on the body part such that the injection patch provides a guide for placing injections at the plurality of injection sites on the particular body part;

engaging a first cartridge with an injection device to select the first cartridge from one of a plurality of cartridges in a tray, the first cartridge containing the solution;

aligning the injection device and the first cartridge with a first location indicator of the plurality of location indicators on the injection patch;

pressing the injection device against the body part, thereby releasing a safety mechanism;

depressing a trigger on the injection device and thereby inserting a needle of the first cartridge through the injection patch at the first location indicator and injecting the solution;

engaging a second cartridge with the injection device to select the second cartridge from one of the plurality of cartridges in the tray, the second cartridge containing the solution;

aligning the injection device and the second cartridge with a second location indicator of the plurality of location indicators on the injection patch;

pressing the injection device against the body thereby releasing the safety mechanism; and depressing the trigger on the injection device and thereby inserting a needle of the second cartridge through the injection patch at the second location indicator and injecting the solution;

wherein each location indicator corresponds to a specific cartridge and wherein corresponding location indicators and cartridges have coordinating identifiers.

14. A method of self-administering an injection of solution, the method comprising:

engaging a cartridge with an injection device to select the cartridge from a tray, the cartridge containing the solution;

positioning an injection patch on a particular body part, wherein the injection patch is shaped for the body part and includes a plurality of openings and each of the openings correlates to one of a plurality of injection sites on the body part, wherein the injection patch includes an adhesive on a contact surface thereof for adhering the injection patch to the body part, and wherein positioning the injection patch includes aligning each of the openings with the correlating injection site on the body part such that the injection patch provides a guide for placing injections at the plurality of injection sites on the body part, wherein each opening is sized and configured to receive a leading edge of the cartridge;

adhering the injection patch to the contact surface;

aligning the injection device and the cartridge with one of the plurality of openings on the injection patch;

pressing the injection device against the body thereby releasing a safety mechanism; and depressing a trigger on the injection device and thereby inserting a needle of the cartridge through the patch at the opening and injecting the solution.

15. The method of claim 14, wherein pressing the injection device against the body part causes the cartridge to come into contact with a body portion of the injection device and thereby release the safety mechanism.

16. The method of claim 14, further comprising:

engaging a second cartridge with the injection device to select the second cartridge from the tray, the second cartridge containing the solution;

aligning the injection device and the second cartridge with a second opening of the plurality of openings on the injection patch;

pressing the injection device against the body part thereby releasing the safety mechanism; and depressing the trigger on the injection device and thereby inserting a needle of the second cartridge through the patch at the second opening of the plurality of openings and injecting the solution.

17. The method of claim 14, wherein the injection patch is shaped as one of a forehead patch or an eye patch.

\* \* \* \* \*